(12) United States Patent
Paul

(10) Patent No.: US 11,737,851 B2
(45) Date of Patent: Aug. 29, 2023

(54) MEDICAL DEVICES FOR MAGNETIC RESONANCE IMAGING AND RELATED METHODS

(71) Applicant: Cook Medical Technologies LLC, Bloomington, IN (US)

(72) Inventor: Ram Paul, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1030 days.

(21) Appl. No.: 16/454,905

(22) Filed: Jun. 27, 2019

(65) Prior Publication Data

US 2020/0000545 A1 Jan. 2, 2020

Related U.S. Application Data

(60) Provisional application No. 62/691,605, filed on Jun. 28, 2018.

(51) Int. Cl.
*A61B 5/05* (2021.01)
*A61B 5/06* (2006.01)
(Continued)

(52) U.S. Cl.
CPC .............. *A61B 90/39* (2016.02); *A61B 5/055* (2013.01); *A61B 5/065* (2013.01);
(Continued)

(58) Field of Classification Search
CPC ........... C21D 7/02; A61B 90/39; A61B 90/37; A61B 5/055; A61B 5/065; A61B 10/0233;
(Continued)

(56) References Cited

U.S. PATENT DOCUMENTS 4,862,891 A 9/1989 Smith
5,169,396 A 12/1992 Dowlatshahi et al.
(Continued)

FOREIGN PATENT DOCUMENTS

CA 2094250 6/1992
DE 202010004107 U1 7/2010
(Continued)

OTHER PUBLICATIONS

Carpenter Technology Corporation. "Magnetic Properties of Stainless Steels," retrieved from Internet May 3, 2018, <URL: https://www.cartech.com/en/alloy-techzone/technical-information/technical-articles/magnetic-properties-of-stainless-steels>, pp. 1-9.
(Continued)

*Primary Examiner* — Bayan Salone
(74) *Attorney, Agent, or Firm* — MacMillan, Sobanski & Todd, LLC

(57) ABSTRACT

Medical devices useful in interventional procedures performed under magnetic resonance imaging (MRI) are described herein. A medical device comprises a body member and a marker formed of work-hardened stainless steel attached to the body member. The stainless steel of the marker has an ultimate tensile strength of between about 100 KSI and about 225 KSI. The marker can be attached to the body member in a manner that contributes work to the stainless steel or in a manner that does not contribute work to the stainless steel. Methods of making medical devices, medical imaging methods, and methods of performing interventional medical treatment are also described herein.

19 Claims, 16 Drawing Sheets

(51) Int. Cl.
  *A61B 10/02* (2006.01)
  *A61B 17/34* (2006.01)
  *C21D 7/02* (2006.01)
  *A61B 90/00* (2016.01)
  *A61B 5/055* (2006.01)

(52) U.S. Cl.
  CPC ...... *A61B 10/0233* (2013.01); *A61B 17/3421* (2013.01); *A61B 90/37* (2016.02); *C21D 7/02* (2013.01); *A61B 17/3403* (2013.01); *A61B 2090/374* (2016.02); *A61B 2090/3933* (2016.02); *A61B 2090/3954* (2016.02); *A61B 2090/3987* (2016.02); *Y10T 29/49826* (2015.01)

(58) Field of Classification Search
  CPC ............ A61B 17/3421; A61B 17/3403; A61B 17/00234; A61B 2017/00831; A61B 2017/00526; A61B 2090/3954; A61B 2090/3987; Y10T 29/49826
  See application file for complete search history.

(56) References Cited

U.S. PATENT DOCUMENTS

| | | | |
|---|---|---|---|
| 5,291,890 A | | 3/1994 | Cline et al. |
| 5,362,478 A | * | 11/1994 | Desai .................. A61K 49/223 |
| | | | 600/431 |
| 5,810,807 A | | 9/1998 | Ganz et al. |
| 6,093,185 A | | 7/2000 | Ellis et al. |
| 6,246,896 B1 | | 6/2001 | Dumoulin et al. |
| 6,267,781 B1 | | 7/2001 | Tu |
| 6,375,059 B2 | | 4/2002 | Ohnishi et al. |
| 6,464,645 B1 | | 10/2002 | Park et al. |
| 6,574,497 B1 | * | 6/2003 | Pacetti ................ G01R 33/285 |
| | | | 600/420 |
| 6,626,849 B2 | | 9/2003 | Huitema et al. |
| 6,687,533 B1 | * | 2/2004 | Hirano .................. A61B 90/39 |
| | | | 424/9.4 |
| 6,695,781 B2 | | 2/2004 | Rabiner et al. |
| 6,772,000 B2 | | 8/2004 | Talpade |
| 6,975,896 B2 | | 12/2005 | Ehnholm et al. |
| 7,160,296 B2 | | 1/2007 | Pearson et al. |
| 7,507,211 B2 | | 3/2009 | Pacetti et al. |
| 7,708,751 B2 | | 5/2010 | Hughes et al. |
| 7,778,682 B2 | | 8/2010 | Kumar et al. |
| 7,875,025 B2 | | 1/2011 | Cockburn et al. |
| 7,943,161 B2 | | 5/2011 | Carlgren et al. |
| 8,049,137 B2 | | 11/2011 | Holman et al. |
| 8,082,021 B2 | | 12/2011 | Hyde et al. |
| 8,142,431 B2 | | 3/2012 | Ducharme |
| 8,167,815 B2 | | 5/2012 | Parihar |
| 8,182,444 B2 | | 5/2012 | Uber, III et al. |
| 8,211,116 B2 | | 7/2012 | Oostman, Jr. et al. |
| 8,214,015 B2 | | 7/2012 | Macaulay et al. |
| 8,257,358 B2 | | 9/2012 | Haddock et al. |
| 8,337,492 B2 | | 12/2012 | Kunis et al. |
| 8,396,532 B2 | | 3/2013 | Jenkins et al. |
| 8,485,992 B2 | | 7/2013 | Griffin et al. |
| 8,521,257 B2 | | 8/2013 | Whitcomb et al. |
| 8,529,872 B2 | | 9/2013 | Frank et al. |
| 8,535,310 B2 | | 9/2013 | Hardin, Jr. et al. |
| 8,740,957 B2 | | 6/2014 | Masotti |
| 8,846,006 B2 | | 9/2014 | Frank et al. |
| 9,326,757 B2 | | 5/2016 | Ravikumar et al. |
| 9,346,093 B2 | | 5/2016 | Cacace |
| 9,669,240 B2 | | 6/2017 | Koehler et al. |
| 9,687,681 B2 | | 6/2017 | Kohler et al. |
| 10,010,723 B2 | | 7/2018 | Koehler |
| 10,172,537 B2 | | 1/2019 | Pfeffer et al. |
| 10,201,333 B2 | | 2/2019 | Nock et al. |
| 10,555,753 B2 | | 2/2020 | Krieger et al. |
| 10,555,756 B2 | | 2/2020 | Krieger et al. |
| 11,142,826 B2 | * | 10/2021 | Han .................... C23C 18/1637 |

| | | | |
|---|---|---|---|
| 2002/0055449 A1 | | 5/2002 | Porta et al. |
| 2002/0058868 A1 | | 5/2002 | Hoshino et al. |
| 2002/0107446 A1 | | 8/2002 | Rabiner et al. |
| 2002/0151787 A1 | | 10/2002 | Bjornerud et al. |
| 2003/0055449 A1 | | 3/2003 | Lee et al. |
| 2003/0060842 A1 | | 3/2003 | Chin et al. |
| 2003/0100828 A1 | | 5/2003 | Engelhard et al. |
| 2004/0082946 A1 | | 4/2004 | Stewart et al. |
| 2004/0200881 A1 | | 10/2004 | Gandy |
| 2004/0254445 A1 | | 12/2004 | Bittner |
| 2006/0073101 A1 | | 4/2006 | Oldfield et al. |
| 2006/0253178 A1 | | 11/2006 | Masotti |
| 2007/0112331 A1 | | 5/2007 | Weber et al. |
| 2007/0149037 A1 | | 6/2007 | Souba et al. |
| 2007/0265551 A1 | | 11/2007 | Pfister |
| 2008/0077085 A1 | | 3/2008 | Eidenschink et al. |
| 2008/0097398 A1 | | 4/2008 | Mitelberg et al. |
| 2009/0264731 A1 | | 10/2009 | Nour et al. |
| 2010/0004562 A1 | * | 1/2010 | Jalisi .................. A61M 25/09 |
| | | | 600/585 |
| 2010/0185080 A1 | | 7/2010 | Myhr |
| 2010/0207291 A1 | | 8/2010 | Eidenschink et al. |
| 2010/0254897 A1 | | 10/2010 | Frank et al. |
| 2010/0268325 A1 | * | 10/2010 | Gregorich ............. A61F 2/3662 |
| | | | 148/559 |
| 2011/0098554 A1 | | 4/2011 | Mardor et al. |
| 2014/0378916 A1 | * | 12/2014 | Simpson ........... A61M 25/0043 |
| | | | 604/264 |
| 2015/0083284 A1 | | 3/2015 | Rawson et al. |
| 2015/0105796 A1 | | 4/2015 | Grace |
| 2015/0182671 A1 | | 7/2015 | Duering |
| 2015/0209551 A1 | | 7/2015 | Burdette et al. |
| 2015/0342580 A1 | | 12/2015 | Clancy |
| 2016/0033059 A1 | | 2/2016 | Fonte |
| 2016/0158509 A1 | | 6/2016 | Wedan et al. |
| 2016/0317212 A1 | | 11/2016 | Ge et al. |
| 2017/0143317 A1 | | 5/2017 | Hoffman |
| 2018/0085027 A1 | | 3/2018 | Kimmel et al. |
| 2018/0303603 A1 | | 10/2018 | Melsheimer et al. |
| 2019/0083071 A1 | | 3/2019 | Rebellino et al. |
| 2019/0167952 A1 | | 6/2019 | Paul, Jr. et al. |
| 2019/0374279 A1 | | 12/2019 | Weitzner et al. |

FOREIGN PATENT DOCUMENTS

| | | | | |
|---|---|---|---|---|
| DE | 202010016473 U1 | | 2/2012 | |
| DE | 202010016473 U1 | * | 4/2012 | ....... A61B 17/00234 |
| DE | 102011101680 A1 | * | 9/2012 | ............ A61B 5/055 |
| DE | 102011101680 A1 | | 9/2012 | |
| EP | 0561903 B1 | | 7/1995 | |
| EP | 0628288 B1 | | 4/2000 | |
| EP | 1116476 A2 | | 7/2001 | |
| EP | 1656963 A1 | | 5/2006 | |
| EP | 1819374 | | 8/2012 | |
| EP | 1819374 B1 | | 8/2012 | |
| EP | 2508213 A1 | | 10/2012 | |
| EP | 2762189 A1 | | 8/2014 | |
| EP | 2508213 B1 | | 3/2018 | |
| EP | 2508213 B1 | | 3/2018 | |
| EP | 3586763 A3 | | 3/2020 | |
| JP | 60-32553 | | 7/1985 | |
| WO | WO2006116538 | | 11/2006 | |
| WO | WO-2006116538 A2 | * | 11/2006 | ............ A61K 49/18 |
| WO | WO2006119645 | | 11/2006 | |
| WO | WO-2006119645 A1 | * | 11/2006 | ............ A61B 5/055 |
| WO | WO2016064753 | | 4/2016 | |
| WO | WO-2016064753 A1 | * | 4/2016 | ............ A61B 5/055 |
| WO | 2018182701 A1 | | 10/2018 | |

OTHER PUBLICATIONS

European Patent Office. Extended European Search Report for European application No. 19183472.0, dated Feb. 13, 2020, pp. 1-12.

Basar et al. "Segmented nitinol guidewires with stiffness-matched connectors for cardiovascular magnetic resonance catheterization: preserved mechanical performance and freedom from heating," J.

(56) References Cited

OTHER PUBLICATIONS

Cardiovascular Magnetic Resonance (2015) 17:105. Published Nov. 30, 2015.
Carpenter Corporation. "Magnetic Properties of Stainless Steels," pp. 1-9. Retrieved from Internet May 3, 2018.
European Patent Office. Partial European Search Report, dated Nov. 6, 2019, pp. 1-14.

* cited by examiner

MEDICAL DEVICES FOR MAGNETIC RESONANCE IMAGING AND RELATED METHODS

CROSS-REFERENCE TO RELATED APPLICATIONS

This application claims the benefit of U.S. Provisional Patent Application No. 62/691,605, filed on Jun. 28, 2018. This related application is incorporated by reference into this disclosure in its entirety.

FIELD

The disclosure relates generally to the field of medical devices. More particularly, the disclosure relates to medical devices useful with magnetic resonance imaging (MRI) equipment and techniques, methods of making medical devices that are useful with MRI equipment and techniques, medical imaging methods, and methods of performing interventional medical treatment.

BACKGROUND

Interventional magnetic resonance is a newly developing field. Widespread use of interventional procedures with MRI depends on several factors, including the availability of markers that can be used with medical devices during interventional procedures to indicate position and other attributes. The prior art includes examples of markers suitable for use with MRI. For example, markers comprising iron oxide particles mixed in a glue, such as a cyanoacrylate, epoxy, or UV curing adhesive, have been described. Associating these markers with medical devices is often labor intensive and difficult to reproduce consistently, rendering medical devices that include them, and the interventional treatments they are intended to support, unreliable and, largely, unaccepted by health care professionals.

A need exists, therefore, for new medical devices useful with MRI equipment and techniques, methods of making medical devices, imaging methods, and methods of performing interventional medical treatment.

SUMMARY OF SELECTED EXAMPLE EMBODIMENTS

Various medical devices, methods of making medical devices, imaging methods, and methods of performing interventional medical treatment are described herein.

An example medical device comprises a body member and a marker attached to the body member, the marker comprising work-hardened stainless steel.

Another example medical device comprises a body member having proximal and distal ends and a stainless steel marker having an ultimate tensile strength of between about 100 KSI and about 225 KSI attached to the body member. Another example medical device comprises a body member having proximal and distal ends and a stainless steel marker having an ultimate tensile strength of between about 150 KSI and about 200 KSI attached to the body member. Another example medical device comprises a body member having proximal and distal ends and a stainless steel marker having an ultimate tensile strength of between about 170 KSI and about 200 KSI attached to the body member. Another example medical device comprises a body member having proximal and distal ends and a stainless steel marker having an ultimate tensile strength of between about 172 KSI and about 197 KSI attached to the body member. Another example medical device comprises a body member having proximal and distal ends and a stainless steel marker having an ultimate tensile strength of between about 187 KSI and about 191 KSI attached to the body member. Another example medical device comprises a body member having proximal and distal ends and a stainless steel marker having an ultimate tensile strength of between about 189 KSI attached to the body member.

Another example medical device comprises a body member and a marker attached to the body member; the body member comprises an elongate rod; the marker comprises a stainless steel tubular member defining a lumen and has an ultimate tensile strength of between about 100 KSI and about 225 KSI; the marker is disposed about the elongate rod such that the elongate rod extends through the lumen of the marker.

Another example medical device comprises a body member and a marker; the body member comprises a tubular member having a wall member having a thickness and defining a body lumen; the wall member defines a passageway that extends into the thickness of the wall member; the marker comprises a stainless steel plug and has an ultimate tensile strength of between about 100 KSI and about 225 KSI; the marker is disposed in the passageway.

Another example medical device comprises a body member and a marker; the body member comprises a tubular member having a wall member having a thickness and defining a body lumen; the wall member defines a passageway that extends through the entire thickness of the wall member; the marker comprises a stainless steel plug and has an ultimate tensile strength of between about 100 KSI and about 225 KSI; the marker is disposed in the passageway.

Another example medical device comprises a body member having proximal and distal ends; the body member comprises a cannula that defines a lumen and a distal tip with a cutting edge on the distal end; a hub member is disposed on the proximal end of the body member; the cannula includes a wall having inner and outer opposing surfaces; a wall thickness extends between the inner and outer surfaces; a passageway extends partially through the thickness of the wall from one of the inner surface and the outer surface; and a marker comprising a stainless steel plug and having an ultimate tensile strength of between about 100 KSI and about 225 KSI is disposed in the passageway.

Another example medical device comprises a body member having proximal and distal ends; the body member comprises a cannula that defines a lumen and a distal tip with a cutting edge on the distal end; a hub member is disposed on the proximal end of the body member; the cannula includes a wall having inner and outer opposing surfaces; a wall thickness extends between the inner and outer surfaces; a passageway extends through the entire thickness of the wall from the inner surface to the outer surface; and a marker comprising a stainless steel plug and having an ultimate tensile strength of between about 100 KSI and about 225 KSI is disposed in the passageway.

Another example medical device includes a first body member and a second body member associated with the first body member; a first stainless steel marker having an ultimate tensile strength of between about 100 KSI and about 225 KSI is attached to the first body member; and a second stainless steel marker having an ultimate tensile strength of between about 100 KSI and about 225 KSI is attached to the second body member.

Another example medical device includes a first body member comprising an elongate member and a second body member comprising a tubular member, the first body member is slidably disposed within the lumen of the second body member; a first stainless steel marker having an ultimate tensile strength of between about 100 KSI and about 225 KSI is attached to the first body member; and a second stainless steel marker having an ultimate tensile strength of between about 100 KSI and about 225 KSI is attached to the second body member.

An example method of making a medical device comprises selecting a medical device precursor having a body member having proximal and distal ends; selecting a marker stock member formed of annealed stainless steel; separating a portion of the marker stock member from the remainder of the marker stock member to form a marker comprising annealed stainless steel; and attaching the marker to the body member in a manner that contributes work to the stainless steel of the marker such that once the attaching step is completed the marker comprises work hardened stainless steel.

Another example method of making a medical device comprises selecting a medical device precursor having a body member having proximal and distal ends; selecting a marker stock member formed of stainless steel; separating a portion of the marker stock member from the remainder of the marker stock member to form a marker; identifying a desired final ultimate tensile strength for the marker; cold working the marker until the marker has a marker ultimate tensile strength that is substantially the same as the final ultimate tensile strength; and attaching the marker to the body member in a manner that does not contribute substantial work to the stainless steel of the marker such that once the attaching step is completed the marker has an ultimate tensile strength that is substantially the final ultimate tensile strength.

Another example method of making a medical device comprises selecting a medical device precursor having a body member having proximal and distal ends; selecting a marker stock member formed of stainless steel having a starting ultimate tensile strength; separating a portion of the marker stock member from the remainder of the marker stock member to form a marker; identifying a desired final ultimate tensile strength for the marker; cold working the marker until the marker has a marker ultimate tensile strength that is greater than the starting ultimate tensile strength but less than the final ultimate tensile strength; and attaching the marker to the body member in a manner that contributes work to the stainless steel of the marker such that once the attaching step is completed the marker has an ultimate tensile strength that is substantially the final ultimate tensile strength.

Another example method of making a medical device comprises selecting a medical device precursor having a body member having proximal and distal ends, a first surface, a second surface, a thickness, and defining a passageway extending from the first surface toward the second surface; selecting a plug of annealed stainless steel; cold working the plug to form a marker; and pressing the marker into the passageway.

Another example method of making a medical device comprises selecting a medical device precursor having a body member having proximal and distal ends, a first surface, a second surface, a thickness, and defining a passageway extending from the first surface toward the second surface; selecting a plug of annealed stainless steel; cold working the plug to form a marker having an ultimate tensile strength between about 100 KSI and about 225 KSI; and pressing the marker into the passageway.

Another example method of making a medical device comprises separating a portion of marker stock from a marker stock member comprising annealed stainless steel; cold working the portion to form a marker having an ultimate tensile strength between about 100 KSI and about 225 KSI; and attaching the marker to a body member of a medical device precursor to form said medical device.

Another example method of making a medical device comprises separating a portion of marker stock from a marker stock member comprising annealed stainless steel; cold working the portion to form a marker having an ultimate tensile strength between about 100 KSI and about 225 KSI; and attaching the marker to a body member of a medical device precursor in a manner that increases the ultimate tensile strength of the marker to form said medical device in which the marker has an ultimate tensile strength of between about 100 KSI and about 225 KSI.

Another example method of making a medical device comprises separating a portion of marker stock from a marker stock member comprising annealed stainless steel; cold working the portion to form a marker having an ultimate tensile strength that is less than about 200 KSI; and attaching the marker to a body member of a medical device precursor in a manner that increases the ultimate tensile strength of the marker to form said medical device in which the marker has an ultimate tensile strength that is greater than about 200 KSI.

An example imaging method comprises selecting a medical device having a body member having proximal and distal ends and comprising a marker formed of work hardened stainless steel; advancing the distal end of the medical device to a first location within a body vessel of a patient and until the marker is disposed at a second location within the body vessel; scanning a portion of the body vessel that includes the first and second locations within the body vessel using a magnetic resonance scanner; obtaining a magnetic resonance image of the portion of the body vessel such that the image includes an artifact indicative of the presence of the marker within the portion of the body vessel; and withdrawing the medical device from the body vessel.

Another example imaging method comprises selecting a medical device having a body member having proximal and distal ends and comprising a stainless steel marker having an ultimate tensile strength of between about 100 KSI and about 225 KSI; advancing the distal end of the medical device to a first location within a body vessel of a patient and until the marker is disposed at a second location within the body vessel; scanning a portion of the body vessel that includes the first and second locations within the body vessel using a magnetic resonance scanner; obtaining a magnetic resonance image of the portion of the body vessel such that the image includes an artifact indicative of the presence of the marker within the portion of the body vessel; and withdrawing the medical device from the body vessel.

An example method of performing an interventional medical treatment comprises selecting a medical device having a body member having proximal and distal ends and comprising a marker formed of work hardened stainless steel; advancing the distal end of the medical device to a first location within a body vessel of a patient and until the marker is disposed at a second location within the body vessel; obtaining a magnetic resonance image of a portion of the body vessel that includes the second location while the marker is disposed at the second location within the body vessel; viewing an artifact in the image generated by the presence of the marker during the obtaining a magnetic resonance image; manipulating the medical device based on the location of the artifact relative to the body vessel; and withdrawing the medical device from the body vessel.

Another example method of performing an interventional medical treatment comprises selecting a medical device having a body member having proximal and distal ends and comprising a stainless steel marker having an ultimate tensile strength of between about 100 KSI and about 225 KSI; advancing the distal end of the medical device to a first location within a body vessel of a patient and until the marker is disposed at a second location within the body vessel; obtaining a magnetic resonance image of a portion of the body vessel that includes the second location while the marker is disposed at the second location within the body vessel; viewing an artifact in the image generated by the presence of the marker during the obtaining a magnetic resonance image; manipulating the medical device based on the location of the artifact relative to the body vessel; and withdrawing the medical device from the body vessel.

Another example method of performing an interventional medical treatment comprises selecting a medical device having a body member having proximal and distal ends and comprising a marker formed of work hardened stainless steel; advancing the distal end of the medical device to a first location within a body vessel of a patient and until the marker is disposed at a second location within the body vessel; obtaining a magnetic resonance image of a portion of the body vessel that includes the second location while the marker is disposed at the second location within the body vessel; determining a location of a portion of the medical device within the body vessel based at least partially on an artifact in the image generated by the presence of the marker during the obtaining a magnetic resonance image; manipulating the medical device within the body vessel; and withdrawing the medical device from the body vessel.

Another method of performing an interventional medical treatment comprises selecting a medical device having a body member having proximal and distal ends and comprising a stainless steel marker having an ultimate tensile strength of between about 100 KSI and about 225 KSI; advancing the distal end of the medical device to a first location within a body vessel of a patient and until the marker is disposed at a second location within the body vessel; obtaining a magnetic resonance image of a portion of the body vessel that includes the second location while the marker is disposed at the second location within the body vessel; determining a location of a portion of the medical device within the body vessel based at least partially on an artifact in the image generated by the presence of the marker during the obtaining a magnetic resonance image; manipulating the medical device within the body vessel; and withdrawing the medical device from the body vessel.

Additional understanding of the claimed invention can be obtained through review of the detailed description of selected example medical devices, methods of making medical devices, imaging methods, and methods of performing interventional medical treatment, below, with reference to the appended drawings.

DETAILED DESCRIPTION OF SELECTED EXAMPLES

Figure 1:
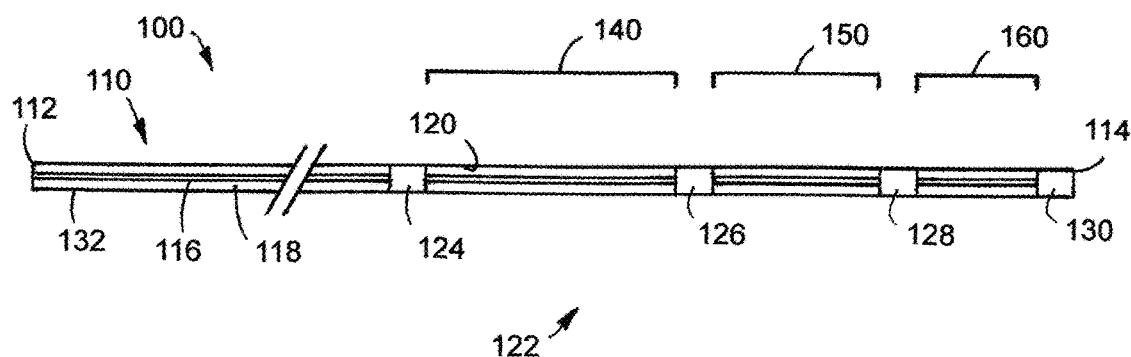
FIG. 1 is a perspective view, partially broken away, of an example medical device.

The following detailed description and the appended drawings describe and illustrate various example medical devices, methods of making medical devices, medical imaging methods, and methods of performing interventional medical treatment. The description and illustration of these examples are provided to enable one skilled in the art to make and use a medical device according to an embodiment of the invention, to practice a method of making a medical device according to an embodiment of the invention, to practice a medical imaging method according to an embodiment of the invention, and to practice a method of performing an interventional medical treatment according to an embodiment of the invention. They are not intended to limit the scope of the invention, or the protection sought, in any manner. The invention is capable of being practiced or carried out in various ways; the examples described and illustrated herein are merely selected examples of these various ways and are not considered exhaustive.

As used herein, the term "attached" refers to one member being secured to another member such that the members do not completely separate from each other during use performed in accordance with the intended use of an item that includes the members in their attached form.

As used herein, the term "KSI" is used as an indicator of units for a quantification of the tensile strength of a material and refers to thousands of pounds per square inch, or kilopounds per square inch.

As used herein, the term "plug" refers to a member having a size and configuration suitable for disposition within a hole, cavity, passageway, or void in another member. The term does not require any particular size or configuration, and the size and configuration of a particular plug will depend on the size and configuration of the hole, cavity, passageway, or void into which the plug is intended to be disposed.

As used herein, the term "stainless steel" refers to a steel alloy having a minimum of 10.5% chromium content by mass.

As used herein, the term "work hardened stainless steel" and grammatically related terms refer to stainless steel that has been hardened by cold working.

Magnetically susceptible materials are typically avoided when developing medical devices for use with MRI equipment and techniques because they can deflect in strong magnetic fields, such as the 1.5 T and 3 T fields used in conventional medical MRI scanners. The possibility for radio-frequency (RF)-induced heating also presents challenges for the use of these materials with MRI equipment and techniques. Furthermore, these materials produce visual artifacts in magnetic resonance images, which can obscure the field of view, and tissues and/or body structures of interest within the field of view, in an MRI scan, reducing the overall value of the procedure.

The inventor has determined, however, that by controlling the magnetic permeability and, optionally, other physical attributes of stainless steel elements used in the making of medical devices, stainless steel markers can produce useful visual artifacts in MRI images. Instead of reducing the overall value of an MRI scan, these visual artifacts dramatically increase the value of a scan by enabling the use of a variety of interventional medical devices and methods. Furthermore, the inventor has determined that by controlling the ultimate tensile strength of stainless steel elements used in the making of medical devices, markers having magnetic permeabilities that produce useful visual artifacts in MRI images as opposed to visual artifacts that negatively impact the utility of MRI images—can be incorporated into medical devices, rendering the medical devices more effective, and more desirable, for MRI techniques. Furthermore, the inventor has determined that by controlling the amount of work put into stainless steel elements used in the making of medical devices, i.e., the extent of cold working performed on the stainless steel, useful and efficient methods of making medical devices that are useful with MRI equipment and techniques are enabled. In turn, controlling the amount of work put into stainless steel elements used in the making of medical devices enables useful imaging methods and methods of performing interventional medical treatment.

FIG. 1 illustrates a first example medical device 100. In this example, the medical device 100 is a guidewire. The medical device includes a body member 110 having proximal 112 and distal 114 ends. The body member 110 includes a mandrel 116 and a stiffening member 118. Each of the mandrel 116 and the stiffening member 118 extends from the proximal end 112 of the body member to the distal end 114 of the body member. The stiffening member 118 defines a lumen 120. The mandrel 116 is disposed within the lumen 120. A plurality of markers 122 is disposed along the axial length of the body member 110. As such, each marker of the plurality of markers 122 is disposed circumferentially about the stiffening member 118. Each marker of the plurality of markers is attached to the body member 110. In the illustrated embodiment, the plurality of markers 122 includes a first marker 124, a second marker 126, a third marker 128, and a fourth marker 130. An outer sheath 132 is disposed over the stiffening member 118 and the plurality of markers 122.

The mandrel 116 can comprise any suitable mandrel. In the illustrated embodiment, the mandrel 116 comprises an elongate member formed of a nickel titanium alloy.

The stiffening member 118 can comprise any suitable member. In the illustrated embodiment, the stiffening member comprises a tubular member defining a lumen 120 into which the mandrel 116 can be disposed. Also, the stiffening member 120 can be formed of any suitable material, such as a polyamide or a polyimide material.

Each marker of the plurality of markers 122 comprises work-hardened stainless steel. Further, each marker of the plurality of markers 122 has properties that produce visual artifacts during MRI procedures in which the medical device 100 is imaged. These visual artifacts can be used to determine placement of the medical device 100 relative to other portions of an MRI image, such as portions of a body vessel into which the medical device 100 has been advanced. The inventor has determined that markers having particular properties produce visual artifacts having sizes and shapes that make them particularly useful in this regard. For example, the inventor has determined that a marker having an ultimate tensile strength between about 100 KSI and about 225 KSI produces particularly useful visual artifacts during MRI procedures in which a medical device that includes the marker is imaged. Indeed, the inventor has determined that, for the medical devices and methods described herein to be useful with MRI equipment and techniques, it is critical for a marker to have an ultimate tensile strength within this range. A marker having an ultimate tensile strength outside of this range provides an unacceptable possibility that the visual artifact produced by the marker in an MRI scan will have a net negative impact on the value of the scan. For example, the visual artifact may be so large as to obscure, to an unacceptable degree or level, other portions of an image generated in the scan. While a marker having an ultimate tensile strength outside of this range produces unacceptable results, the inventor has determined that a marker having an ultimate tensile strength within a narrower range can produce visual artifacts having the same or better usefulness as a marker having an ultimate tensile strength between about 100 KSI and about 225 KSI. Indeed, the inventor has determined that a marker having an ultimate tensile strength between about 150 KSI and about 200 KSI produces particularly useful visual artifacts during MRI procedures in which a medical device that includes the marker is imaged. Furthermore, the inventor has determined that a marker having an ultimate tensile strength between about 170 KSI and about 200 KSI produces particularly useful visual artifacts during MRI procedures in which a medical device that includes the marker is imaged. Furthermore, the inventor has determined that a marker having an ultimate tensile strength between about 172 KSI and about 197 KSI produces particularly useful visual artifacts during MRI procedures in which a medical device that includes the marker is imaged. Furthermore, the inventor has determined that a marker having an ultimate tensile strength between about 187 KSI and about 191 KSI produces particularly useful visual artifacts during MRI procedures in which a medical device that includes the marker is imaged. Furthermore, the inventor has determined that a marker having an ultimate tensile strength of about 189 KSI produces particularly useful visual artifacts during MRI procedures in which a medical device that includes the marker is imaged.

The mass of each marker also contributes to the visual artifact produced by the marker during MRI scans. It is important to balance the mass of each marker, and the total mass of all markers in a medical device according to an embodiment, with performance considerations for the medical device, though, such as handling, pushability, and torqueability. The inventor has determined that a marker having a mass of between about 0.05 mg and about 2.74 mg produces particularly useful visual artifacts. While a marker having a mass outside of this range increases the possibility that the marker will negatively impact the performance considerations mentioned above, the inventor has determined that a marker having a mass within a narrower range can produce visual artifacts having the same or better usefulness as a marker having a mass of between about 0.05 mg and about 2.74 mg. Indeed, the inventor has determined that a marker having a mass of between about 0.1 mg and about 1.37 mg produces particularly useful visual artifacts while not negatively impacting performance considerations of the medical device in any appreciable manner. The inventor has determined that a marker having a mass of between about 0.15 mg and about 0.685 mg produces particularly useful visual artifacts while not negatively impacting performance considerations of the medical device in any appreciable manner. Furthermore, the inventor has determined that a marker having a mass of about 0.15 mg produces particularly useful visual artifacts while not negatively impacting performance considerations of the medical device in any appreciable manner.

In some embodiments, a marker is incorporated into a medical device based on both ultimate tensile strength and mass considerations. Indeed, the inventor has determined that a marker having an ultimate tensile strength between about 100 KSI and about 225 KSI and a mass between about 0.34 mg and about 2.74 mg produces particularly useful visual artifacts during MRI procedures in which a medical device that includes the marker is imaged. Furthermore, the inventor has determined that a marker having an ultimate tensile strength between about 150 KSI and about 200 KSI and a mass between about 0.69 mg and about 2.05 mg produces particularly useful visual artifacts during MRI procedures in which a medical device that includes the marker is imaged. Furthermore, the inventor has determined that a marker having an ultimate tensile strength between about 170 KSI and about 200 KSI and a mass between about 0.69 mg and about 2.05 mg produces particularly useful visual artifacts during MRI procedures in which a medical device that includes the marker is imaged. Furthermore, the inventor has determined that a marker having an ultimate tensile strength between about 172 KSI and about 197 KSI and a mass between about 0.69 mg and about 2.05 mg produces particularly useful visual artifacts during MRI procedures in which a medical device that includes the marker is imaged. Furthermore, the inventor has determined that a marker having an ultimate tensile strength between about 187 KSI and about 191 KSI and a mass between about 0.69 mg and about 2.05 mg produces particularly useful visual artifacts during MRI procedures in which a medical device that includes the marker is imaged. Furthermore, the inventor has determined that a marker having an ultimate tensile strength of about 189 KSI and a mass of about 1.37 mg produces particularly useful visual artifacts during MRI procedures in which a medical device that includes the marker is imaged.

Spatial and other considerations can guide the selection of a suitable mass and ultimate tensile strength for a particular marker in a particular medical device. For example, the inventor has determined that selection of a marker having a mass in a lower portion of the range of between about 0.05 mg and about 2.74 mg, e.g., less than about 1 mg, but an ultimate tensile strength in a higher portion of the range of between about 100 KSI and about 225 KSI, e.g., greater than about 175 KSI, can produce particularly useful visual artifacts, especially for markers in medical devices in which it may be difficult to place large markers. For example, the inventor believes a marker having a mass of about 0.15 mg and an ultimate tensile strength of about 189 KSI will produce beneficial visual artifacts as a plug placed in the distal end of a guidewire or in the wall of a cannula. As described in detail below, the overall length of a marker also contributes to the visual artifact produced by the marker during MRI scans. For this particular example, the inventor has determined that a length of about 0.4 mm provides a marker that is large enough to be conveniently handled during manufacturing but, yet, is not so large as to produce dephasing in blood, as described below. Conversely, the inventor has determined that selection of a marker having a mass in a higher portion of the range of between about 0.05 mg and about 2.74 mg, e.g., greater than about 1 mg, but an ultimate tensile strength in a lower portion of the range of between about 100 KSI and about 225 KSI, e.g., less than about 197 KSI, can produce particularly useful visual artifacts, especially for markers in medical devices in which it may be difficult to place small markers or for which handling of small markers during manufacturing is a primary concern.

It is noted that a closely associated group of markers can be used to achieve a similar visual artifact to that produced by a single marker. For example, three markers having desired ultimate tensile strengths can be attached to a medical device in a manner that forms a group of closely associated markers on the medical device such that the markers produce a desired visual artifact, as a group, during MRI scans. Any suitable number of markers can be used in a group of this sort, including two markers, more than two markers, three markers, a plurality of markers, four markers, five markers, and more than five markers. Also, markers can be selected based on their contribution to a desired overall mass of a marker load. For example, in the example listed above in which it is desirable to have a marker having a mass of about 0.15 mg and an ultimate tensile strength of about 189 KSI, a marker group comprising three separate markers, each having a mass of about 0.05 mg and an ultimate tensile strength of about 189 KSI can be used as a substitute for a single marker having a mass of about 0.15 mg and an ultimate tensile strength of about 189 KSI. It is expected that the marker group, when attached to the medical device in a manner that forms a group of closely associated markers, will produce a visual artifact in an MRI scan that is similar to the visual artifact produced by the single marker In these embodiments, it is important that the individual markers in the marker group be positioned relative to each other such that the group produces a visual artifact that is similar to the visual artifact produced by the single marker. If the individual markers in the marker group are positioned too far from each other, such that they are not sufficiently closely associated, the visual artifact produced by the group will potentially become separate visual artifacts and may obscure portions of images obtained in MRI scans.

The overall length of each marker also contributes to the visual artifact produced by the marker during MRI scans. Similar to the mass considerations above, it is important to balance the length of each marker, and the total length of all markers in a medical device according to an embodiment, with performance considerations, though, such as handling, pushability, and torqueability. Also, markers of excessive length can result in dephasing of blood, for example. The inventor has determined that a marker having a length of between about 0.25 mm and about 2.0 mm produces particularly useful visual artifacts during MRI procedures in which a medical device that includes the marker is imaged. Furthermore, the inventor has determined that a marker having a length of between about 0.5 mm and about 1.5 mm produces particularly useful visual artifacts during MRI procedures in which a medical device that includes the marker is imaged. Furthermore, the inventor has determined that a marker having a length of about 1.0 mm produces particularly useful visual artifacts during MRI procedures in which a medical device that includes the marker is imaged. Furthermore, the inventor has determined that a marker having a length of about 0.5 mm produces particularly useful visual artifacts during MRI procedures in which a medical device that includes the marker is imaged. The inventor has determined that markers having a length of greater than 2.0 mm can produce visual artifacts during MRI procedures that are too large to be useful for particular applications.

Each marker of the plurality of markers 122 can be attached to the body member in any suitable manner. In the illustrated embodiment, each of the markers 124, 126, 128, 130 has been attached to the body member 110 in a manner that did not contribute work to the stainless steel. In other words, each of the markers 124, 126, 128, 130 has been attached to the body member 110 in a manner that did not increase the ultimate tensile strength of the stainless steel in the marker. This arrangement is considered suitable when the markers comprise work hardened stainless steel having a final desired ultimate tensile strength and magnetic permeability. For medical devices in which this arrangement is desirable, the markers can be attached to the body member in any suitable manner that does not contribute work to the work hardened stainless steel of the markers. In the illustrated embodiment, each of the markers 124, 126, 128, 130 is attached to the body member 110 by an adhesive disposed between the marker and the stiffening member 118. In these embodiments, any adhesive considered suitable for inclusion in medical devices can be used.

Each marker of the plurality of markers 122 can have any suitable configuration. In the illustrated embodiment, each marker 124, 126, 128, 130 comprises a tubular member defining a marker lumen. Tubular markers can be disposed around a portion of the body member 110 of the medical device 100. As illustrated in FIG. 1, tubular markers 124, 126, 128, 130 can be disposed around the stiffening member 118 such that each marker 124, 126, 128, 130 extends around the entire circumference of the stiffening member 118. Alternatively, a marker that defines a partial circumference can be disposed around the body member of a medical device according to an embodiment such that the marker extends around only a portion of the circumference of the body member.

Any suitable number of markers can be used in a medical device according to an embodiment. While the first example medical device includes four markers 124, 126, 128, 130, it is to be appreciated that a medical device according to an embodiment can include any number of markers considered suitable for the intended use of the particular medical device. Examples of suitable numbers of markers for inclusion in a medical device according to an embodiment include one marker, two markers, more than two markers, three markers, a plurality of markers, four markers, five markers, six markers, seven markers, eight markers, nine markers, ten markers, and more than ten markers. Furthermore, in embodiments that include two or more markers, the markers can be spaced from each other by a desired distance. It should be noted, though, that, because the markers produce visual artifacts and their utility in the medical device is based on this production of visual artifacts in MRI procedures, it is important to space markers from each other by a distance that does not result in overlapping or nearly overlapping visual artifacts. If markers are spaced too closely to each other in a medical device, the usefulness of the markers can be lost as the visual artifacts produced by individual markers overlap or nearly overlap. If this occurs, the obscuring nature of the overlapping or nearly overlapping visual artifacts may outweigh any benefit provided by their presence. The inventor has determined that, in a medical device having a first marker and a second marker, such as the guidewire illustrated as the medical device 100 in FIG. 1, it is advantageous to space the first marker from the second marker by a distance of between about 5 cm and about 100 cm. Furthermore, the inventor has determined that, in a medical device having a first marker and a second marker, it is advantageous to space the first marker from the second marker by a distance of between about 5 cm and about 10 cm. Furthermore, the inventor has determined that, in a medical device having a first marker and a second marker, it is advantageous to space the first marker from the second marker by a distance of greater than about 10 cm. Furthermore, the inventor has determined that, in a medical device having a first marker and a second marker, it is advantageous to space the first marker from the second marker by a distance of about 10 cm. Furthermore, the inventor has determined that, in a medical device having a first marker and a second marker, it is advantageous to space the first marker from the second marker by a distance of greater than about 5 cm. Furthermore, the inventor has determined that, in a medical device having a first marker and a second marker, it is advantageous to space the first marker from the second marker by a distance of about 5 cm. The inventor has determined that markers separated by a distance of less than about 5 cm may produce visual artifacts that are too close to each other to be useful for particular applications.

Also, in a medical device having three markers, the first marker can be spaced from the second marker by a first distance and the second marker can be spaced from the third marker by a second distance. The first and second distances can be the same or can be different. The inventor has determined that regular spacing between markers in a medical device according to a particular embodiment can be advantageous because the markers are visualized via the visual artifacts they produce in MRI. As such, a regular pattern of artifacts can enhance the usefulness of the markers in these procedures. Nevertheless, irregular spacing between some or all markers in a medical device according to a particular embodiment that includes multiple markers can be used as well. For example, in the illustrated embodiment, first 124 and second 126 markers are spaced from each other by a first distance 140, second 126 and third 128 markers are spaced from each other by a second distance 150, and third 128 and fourth 130 markers are spaced from each other by a third distance 160. Each of the first 140, second 150, and third 160 distances is different from the other distances.

The outer sheath 132 can have any suitable configuration. For example, in the illustrated embodiment, the outer sheath 132 comprises a polymeric sheath that has been placed over the stiffening member 118 such that it extends over the stiffening member 118 and the plurality of markers 122. Alternatively, the outer sheath 132 can comprise a coating or other suitable configuration. For example, the outer sheath 132 can comprise a polymeric coating applied to the stiffening member or another element, forming a jacket on the element.

Figure 2:
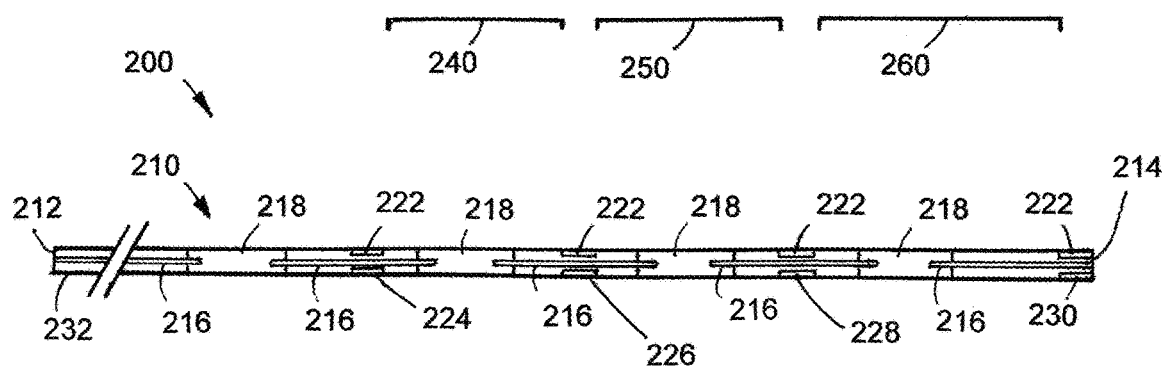
FIG. 2 is a sectional view, partially broken away, of another example medical device.

FIG. 2 illustrates a second example medical device 200. In this example, the medical device 200 is a segmented guidewire. The medical device 200 includes a body member 210 having proximal 212 and distal 214 ends. The body member 210 includes a plurality of rods 216 and a plurality of connectors 218. Each connector of the plurality of connectors 218 is disposed between and connects a pair of adjacent rods of the plurality of rods 216. A plurality of markers 222 is disposed along the axial length of the body member 210. Each marker of the plurality of markers 222 is disposed circumferentially about one of the rods of the plurality of rods 216. As such, each marker of the plurality of markers 222 is attached to the body member 210. In the illustrated embodiment, the plurality of markers 222 includes a first marker 224, a second marker 226, a third marker 228, and a fourth marker 230. An outer sheath 232 is disposed over the plurality of rods 216, the plurality of connectors 218, and the plurality of markers 222.

Each rod of the plurality of rods 216 advantageously comprises a metal, such as nitinol or another alloy. Importantly, though, the axial length of each rod of the plurality of rods 216 is short enough that the rod is non-resonant during an MRI procedure. For example, for medical devices intended to be used with a 1.5 T MRI scanner, each rod should have an axial length that is less than 10 cm. For medical devices intended to be used with a 3.0 T MRI scanner, each rod should have an axial length that is less than 5 cm. Each connector of the plurality of connectors 218 advantageously comprises a non-metallic, insulative material, such as a polymeric material. Alternatively, each connector of the plurality of connectors 218 can comprise a metal that is coated with a non-metallic, insulative material. Also alternatively, in some embodiments, rods can comprise a metal that has been coated with a non-metallic, insulative material and the connectors can comprise a metal, a non-metallic material, or a metal coated with a non-metallic, insulative material.

In the illustrated embodiment, each of the markers 224, 226, 228, 230 has been attached to the body member 210 in a manner that contributed work to the stainless steel of which the marker is formed such that, in the final medical device 200, each of the markers 224, 226, 228, 230 comprises work hardened stainless steel. In other words, each of the markers 224, 226, 228, 230 has been attached to the body member 210 in a manner that increased the ultimate tensile strength of the stainless steel in the marker. This arrangement is considered suitable when the markers are formed of a stainless steel that does not have a final desired ultimate tensile strength and magnetic permeability. For medical devices in which this arrangement is desirable, the markers can be attached to the body member in any suitable manner that contributes work to the stainless steel of the markers such that, in the final medical device, each of the markers comprises work hardened stainless steel. Any cold working process can be used, including crimping, swaging, hammering, pressing, pinning, and dimpling. In the illustrated embodiment, each of the markers 224, 226, 228, 230 has been crimped onto one of the plurality of rods 216 of the body member 210. Other attachments for the markers 224, 226, 228, 230 are possible. For example, one or more of the markers 224, 226, 228, 230 can be attached to the body member 210 at a junction of a rod 216 and a connector 218.

The medical device 200 of this embodiment includes a regular spacing between markers 224, 226, and 228. As illustrated in FIG. 2, first 224 and second 226 markers are spaced from each other by a first distance 240 and second 226 and third 228 markers are spaced from each other by a second distance 250. The first distance 240 is the same as the second distance 250. Third 228 and fourth 230 markers are spaced from each other by a third distance 260 that is different from the first 240 and second 250 distances. In the illustrated embodiment, the third distance 260 is greater than the first 240 and second 250 distances.

While the first example medical device 100 only includes markers 124, 126, 128, 130 attached to the body member 110 of the medical device 100 in a manner that did not contribute work to the stainless steel of the individual markers 124, 126, 128, 130, and the second example medical device 200 only includes markers 224, 226, 228, 230 attached to the body member 210 of the medical device 200 in a manner that did contribute work to the stainless steel of the individual markers 224, 226, 228, 230, it is noted that a medical device according to a particular embodiment may include one or more markers attached to a body member of the medical device in a manner that did not contribute work to the stainless steel of the marker or markers and also include one or more markers attached to a body member of the medical device in a manner that did contribute work to the stainless steel of the marker or markers. In other words, a medical device according to a particular embodiment may include one or more markers attached to a body member of the medical device in a manner that did not increase the ultimate tensile strength of the stainless steel of the marker or markers and also include one or more markers attached to a body member of the medical device in a manner that did increase the ultimate tensile strength stainless steel of the marker or markers. For example, a medical device according to a particular embodiment may include a first marker that has been adhered to a body member and a second marker that has been crimped onto the same body member or another body member of the medical device. This configuration may be useful in medical devices that include multiple body members, each of which may benefit from the presence of a marker that produces a useful visual artifact in MRI images. For example, a catheter having an elongate member, such as a dilator or other core member, slidably disposed within an outer sheath member can include one or more markers attached to the core member in a manner that adds work to the stainless steel of the marker, and can also include one or more markers attached to the outer sheath member in a manner that does not add work to the stainless steel of the marker. The reverse arrangement, of course, is also possible. For example, a catheter can include one or more markers attached to the core member in a manner that does not add work to the stainless steel of the marker and can also include one or more markers attached to the outer sheath member in a manner that adds work to the stainless steel of the marker.

Figure 3:
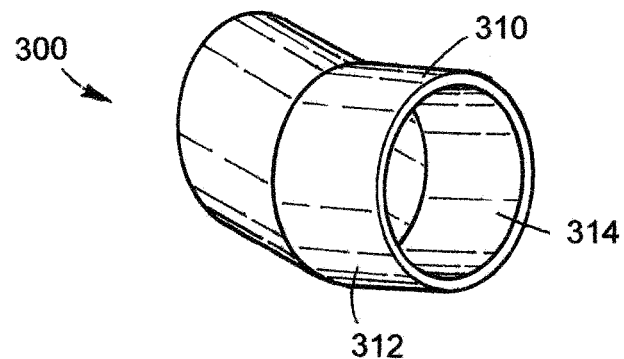
FIG. 3 is a perspective view of an example marker suitable for use in a medical device according to an embodiment.

FIG. 3 illustrates an example marker 300 suitable for use in a medical device according to an embodiment. The marker is a short tubular member 310 having an outer surface 312 and defining a marker lumen 314. The marker lumen 314, for the illustrated marker, defines a substantially circular cross-sectional shape. It is noted, though, that a marker lumen for a marker used in a medical device according to an embodiment may define a different cross-sectional shape. For example, in a medical device according to an embodiment in which a marker is attached to the body member in a manner that contributes work to the stainless steel of the marker, the marker lumen may define a substantially ovoid cross-sectional shape or a substantially rectangular cross-sectional shape. In these embodiments, a marker having a lumen defining a substantially circular cross-sectional shape, such as the marker 300 illustrated in FIG. 3, can be disposed on the body member of the medical device and subsequently attached to the body member using a technique, such as crimping or swaging the marker to the body member, that contributes work to the stainless steel of the marker. Also, while the illustrated marker 300 defines an angled tubular member, it is noted that other tubular configurations are suitable for use as markers in medical devices according to embodiments of the invention. For example, straight, substantially straight, and curved tubular members can be used.

Figure 4:
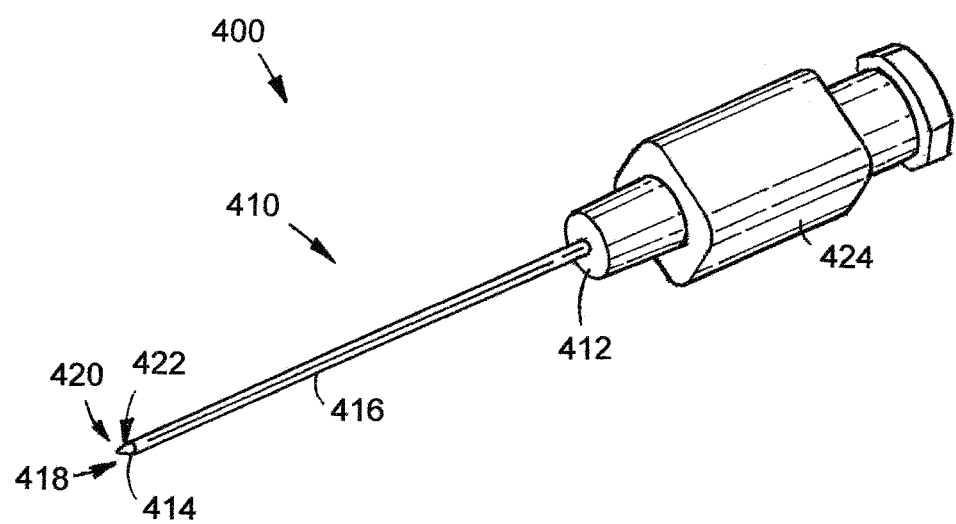
FIG. 4 is a perspective view of another example medical device.
Figure 5:
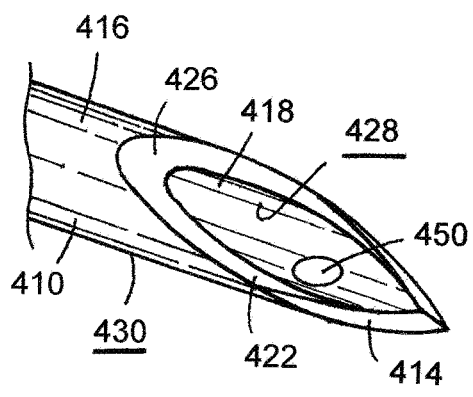
FIG. 5 is a magnified view of the distal end of the medical device illustrated in FIG. 4.
Figure 5A:
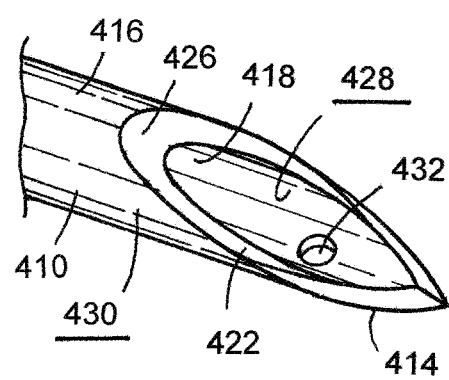
FIG. 5A is a magnified view of the distal end of the medical device illustrated in FIG. 4 before the marker has been attached to the body member of the medical device.

FIGS. 4, 5, and 5A illustrate a third example medical device 400. In this example, the medical device 400 is a needle. The medical device 400 includes a body member 410 having a proximal end 412 and a distal end 414. In this embodiment, the body member is a cannula 416 that defines a lumen 418 and a distal tip 420 with a cutting edge 422 on the distal end 414. A hub member 424 is disposed on the proximal end 412 of the body member 410. As best illustrated in FIG. 5, a marker 450 is attached to the cannula 418 and, as such, to the body member 410.

As best illustrated in FIG. 5, the cannula 418 includes a wall 426 having inner 428 and outer 430 opposing surfaces. A wall thickness extends between the inner 428 and outer 430 surfaces. As best illustrated in FIG. 5A, which illustrates the distal end of the medical device 400 without the marker 450, a passageway 432 extends through the entire thickness of the wall 426, from the inner surface 428 to the outer surface 430. Alternatively, the passageway can extend only partially through the thickness of the wall 426, either from the inner surface 428 toward the outer surface 430 or from the outer surface 430 toward the inner surface 428.

In this embodiment, the marker 450 is a plug disposed within the passageway 432. Also, as best illustrated in FIG. 5, the marker 450 is flush with the inner surface 428 and the outer surface 430. Also in this embodiment, the marker 450 has been attached to the body member 410 in a manner that contributes work to the stainless steel of the marker such that, in the final medical device 400, the marker 450 comprises work hardened stainless steel. In this embodiment, the marker 450 has been pressed into the passageway 432. The friction fit between the wall 426 and marker 450, and the force required to press the marker 450 into the passageway 432, may be sufficient to achieve the desired ultimate tensile strength for the stainless steel of the marker 450 and attachment to the body member 410. Additional securement can be used, if desired. For example, the marker 432 can be laser welded to the wall 426 to secure the marker 450 in the passageway 432.

In other medical device embodiments, one or more filaments of cold-worked stainless steel having a known ultimate tensile strength are placed within a medical device. For example, a plurality of filaments can be embedded in a doping matrix that is included in a medical device, such as part of a guidewire. In another example, one or more filaments are laid along a portion of a medical device, such as a guidewire or coated guidewire, and then covered with a polymer to sandwich the filament or filaments between the guidewire or coated guidewire and the polymer coating. In these embodiments, the filaments can be positioned axially along the portion of the medical device, or wrapped helically around the portion of the medical device. In these embodiments, relatively short filaments of a relatively small diameter, such as filaments having a length of about 10 cm or less and a diameter of about 25 microns or less. When made of stainless steel, this provides a filament having a mass of about 0.4 mg. When formed of stainless steel having an appropriate and desirable ultimate tensile strength as described herein, such as less than about 200 KSI, these filaments can serve as effective artifact generating markers as described herein. In these embodiments, if multiple filaments are used within the same medical device, it is considered important to space the filaments from each other on the medical device such that a gap is formed between each pairing of filaments, thereby avoiding the formation of a conductive path between filaments. In these embodiments, a gap of at least a few thousandths of an inch is considered suitable. In all embodiments that include filaments, the filaments can have a round cross-sectional profile or a flat cross-sectional profile, such as a square or rectangular cross-sectional profile.

Various methods of making medical devices, imaging methods, and methods of performing interventional medical treatment are described herein. While the methods described herein are shown and described as a series of acts, it is to be understood and appreciated that the methods are not limited by the order of acts except as indicated, as some acts may, in accordance with these methods, occur in different orders, and/or concurrently with other acts described herein.

Figure 6:
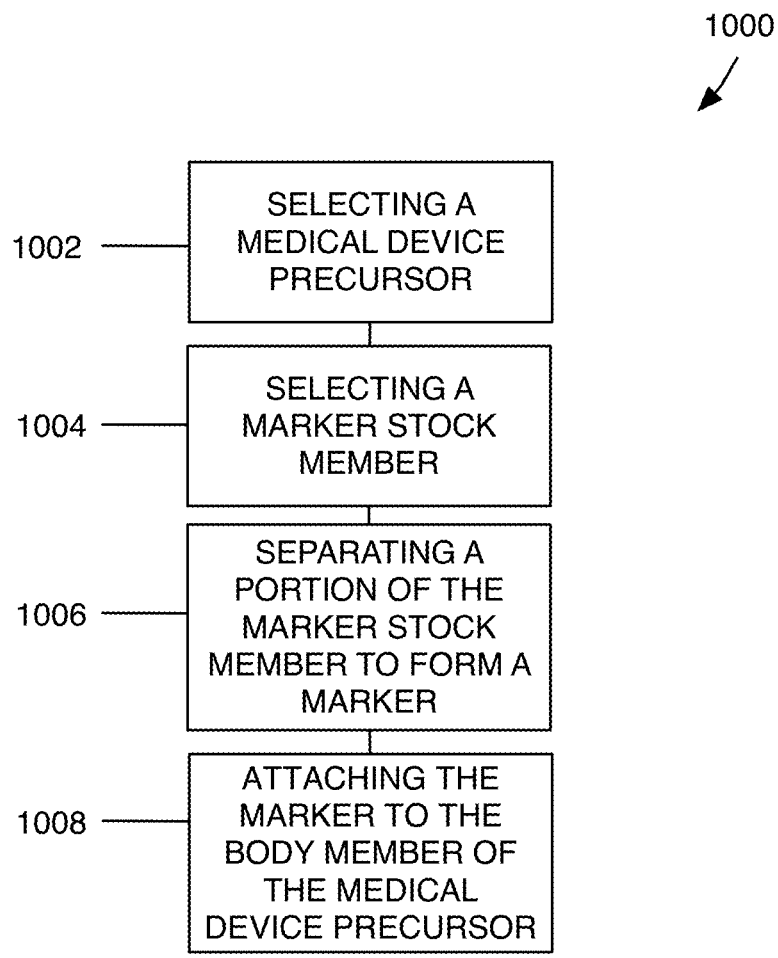
FIG. 6 is a schematic illustration of an example method of making a medical device.

FIG. 6 is a schematic illustration of an example method 1000 of making a medical device. An initial step 1002 comprises selecting a medical device precursor having a body member having proximal and distal ends. Another step 1004 comprises selecting a marker stock member formed of annealed stainless steel. Another step 1006 comprises separating a portion of the marker stock member from the remainder of the marker stock member to form a marker comprising annealed stainless steel. Another step 1008 comprises attaching the marker to the body member in a manner that contributes work to the stainless steel of the marker such that once the attaching step 1008 is completed the marker comprises work hardened stainless steel. In other words, step 1008 comprises attaching the marker to the body member in a manner that increases the ultimate tensile strength of the stainless steel of the marker.

The step 1002 of selecting a medical device precursor can be accomplished by identifying a medical device or a medical device for which it is desirable to attach a marker for purposes of using the medical device with magnetic resonance imaging. The medical device can be any suitable medical device, or a precursor to such a medical device. Examples of suitable medical devices include guidewires, catheters, needles, sheaths, snares, and other suitable interventional medical devices. Also, implantable medical devices, such as stents, frames, valves, filters, occluders, and other devices can be selected in this step as well.

The step 1004 of selecting a marker stock member can be accomplished by identifying a marker stock member of annealed stainless steel having dimensions suitable for use, with modification in subsequent steps, as a marker for the medical device identified in step 1002. For this step in this example method, it is important that the stainless steel is annealed, as the cold working completed in the attaching step 1008 contributes the work needed to produce the desired visual artifact. Examples of suitable types of marker stock members include rods, ribbons, bars, and tubular members. The specific type of marker stock member selected in a particular method of making a medical device will depend on various considerations, including the nature of the medical device being made. For example, if the medical device being made includes an elongate member, such as a rod, strut, or other elongate member, a tubular marker stock member may be selected to allow a marker formed from the marker stock member to be disposed circumferentially about the rod member or other elongate member of the medical device. Similarly, if the medical device being made includes a passageway in a wall member, for example, a rod marker stock member may be selected to allow a marker formed from the marker stock member to be disposed in the passageway of the medical device as a plug.

The step 1006 of separating a portion of the marker stock member from the remainder of the marker stock member can be accomplished by cutting a portion of the marker stock member from the remainder of the marker stock member, such as by laser cutting or other suitable technique. For this step in this example method, it is important that the separating be performed in a manner that does not contribute work to the stainless steel of the portion of the marker stock member being separated from the remainder of the marker stock member. Laser cutting and similar techniques are considered suitable for this reason; crimping, folding, and other cold working techniques are not considered suitable for the same reason.

The step 1008 of attaching the marker to the body member in a manner that contributes work to the stainless steel of the marker can be accomplished in any suitable manner that cold works the marker, formed in the separating step 1006, such that the stainless steel in the marker, once the step 1008 of attaching is completed, comprises work hardened stainless steel. Examples of suitable cold working techniques include crimping, swaging, hammering, pressing, pinning, and dimpling. The technique chosen for a particular method of making a medical device will depend on various considerations, including the nature of the medical device being made and the nature of the marker formed in step 1006. For this particular method, for example, if the marker formed in step 1006 is a tubular member defining a lumen or a member defining a partial circumference, such as a c-shaped member, and the medical device being made includes an elongate member, such as a rod, strut, or other elongate member, the marker can be attached to the body member of the medical device precursor by disposing the marker circumferentially about the elongate member of the medical device and crimping the marker onto the elongate member. Also, if the marker formed in step 1006 is a rod, plug, or other non-lumen defining member and the medical device being made includes a wall member or other portion defining a passageway, the marker can be attached to the body member of the medical device precursor by forcing the marker into the passageway by pushing, hammering, or otherwise forcing the marker into the passageway.

No matter the technique chosen for step 1008 in a method according to a particular embodiment, it is considered important that the step 1008 of attaching the marker to the body member be performed such that the stainless steel of the marker, once step 1008 is completed, has an ultimate tensile strength of between about 100 KSI and about 225 KSI. Furthermore, the inventor has determined that performing this step 1008 until the stainless steel of the marker has an ultimate tensile strength of between about 150 KSI and about 200 KSI is advantageous. Furthermore, the inventor has determined that performing this step 1008 until the stainless steel of the marker has an ultimate tensile strength of between about 170 KSI and about 200 KSI is advantageous. Furthermore, the inventor has determined that performing this step 1008 until the stainless steel of the marker has an ultimate tensile strength of between about 172 KSI and about 197 KSI is advantageous. Furthermore, the inventor has determined that performing this step 1008 until the stainless steel of the marker has an ultimate tensile strength of between about 187 KSI and about 191 KSI is advantageous. Furthermore, the inventor has determined that performing this step 1008 until the stainless steel of the marker has an ultimate tensile strength of about 189 KSI is advantageous.

To determine whether step 1008 has been performed to an appropriate degree, the ultimate tensile strength of the marker can be determined in any suitable manner. For example, a hardness determination can be made, such as a HV Vickers hardness or other suitable hardness determination, and a correlation to ultimate tensile strength can then be made using known conversion factors. This approach can be used to assess the ultimate tensile strength of a marker in medical devices and methods according to embodiments. It is noted that, if a marker must be removed from a medical device to have its ultimate tensile strength determined, the removal should be done in a manner that does not input additional work into the stainless steel of the marker. That is, the removal should be done in a mAnner that does not itself increase the ultimate tensile strength of the marker.

Figure 7:
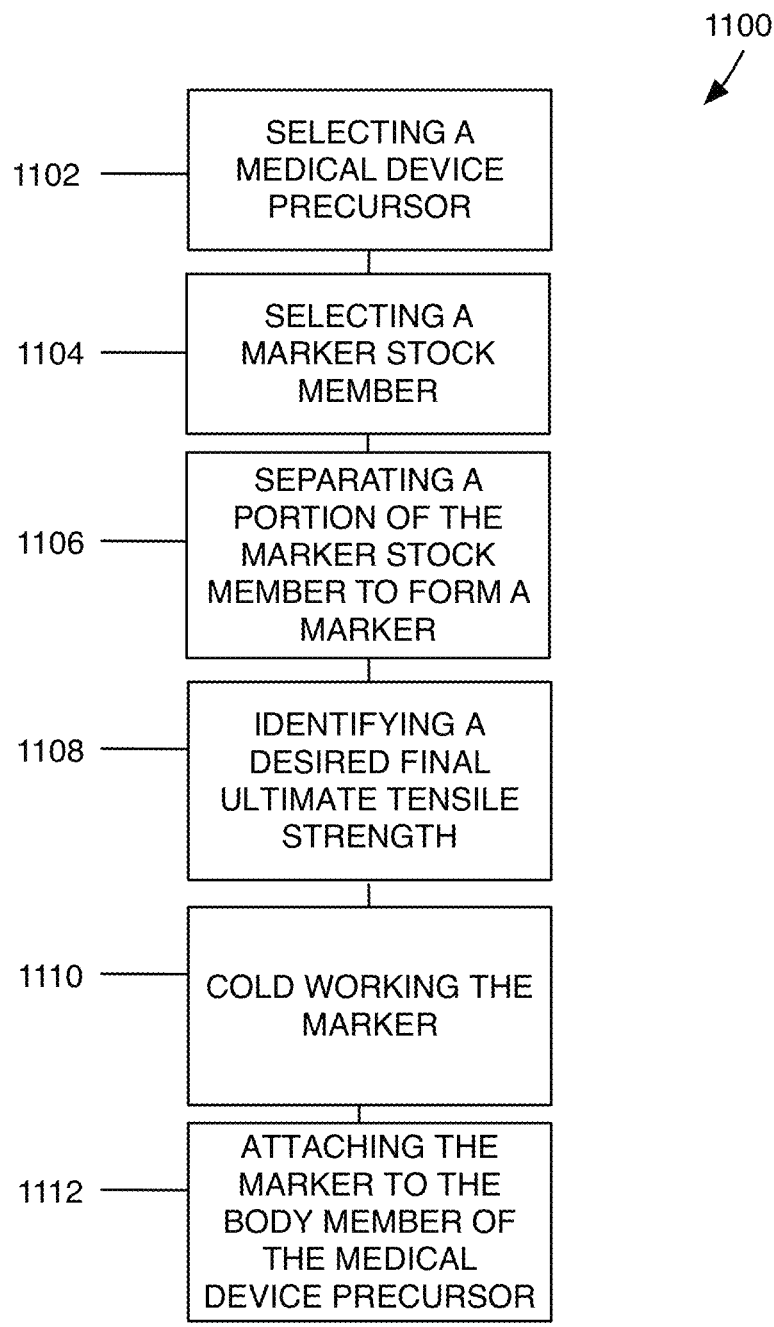
FIG. 7 is a schematic illustration of another example method of making a medical device.

FIG. 7 is a schematic illustration of another example method 1100 of making a medical device. An initial step 1102 comprises selecting a medical device precursor having a body member having proximal and distal ends. Another step 1104 comprises selecting a marker stock member formed of stainless steel. Another step 1106 comprises separating a portion of the marker stock member from the remainder of the marker stock member to form a marker. Another step 1108 comprises identifying a desired final ultimate tensile strength for the marker. Another step 1110 comprises cold working the marker until the marker has a marker ultimate tensile strength that is substantially the same as the final ultimate tensile strength identified in step 1108. Another step 1112 comprises attaching the marker to the body member in a manner that does not contribute substantial work to the stainless steel of the marker such that once the attaching step 1112 is completed the ultimate tensile strength of the marker is substantially the ultimate tensile strength identified in step 1108.

The step 1102 of selecting a medical device precursor can be accomplished by identifying a medical device or a medical device for which it is desirable to attach a marker for purposes of using the medical device with magnetic resonance imaging. The medical device can be any suitable medical device, or a precursor to such a medical device. Examples of suitable medical devices include guidewires, catheters, needles, sheaths, snares, and other suitable interventional medical devices. Also, implantable medical devices, such as stents, frames, valves, filters, occluders, and other devices can be selected in this step as well. A medical device precursor can comprise any structural member that can precede a finished medical device in a method of making a medical device, such as a frame, a wire, a rod, a sheath, and other suitable structural members.

The step 1104 of selecting a marker stock member can be accomplished by identifying a marker stock member of stainless steel having dimensions suitable for use, with modification in subsequent steps, as a marker for the medical device identified in step 1002. For this step in this example method, the stainless steel can be annealed, as the cold working completed in subsequent step 1110 contributes the work needed to produce the desired visual artifact. Importantly, though, for this step in this example method, the stainless steel can be non-annealed as long as the stainless steel has an ultimate tensile strength that allows for the input of work via cold working to achieve the desired final ultimate tensile strength in subsequent steps. Examples of suitable types of marker stock members include rods, ribbons, bars, and tubular members. The specific type of marker stock member selected in a particular method of making a medical device will depend on various considerations, including the nature of the medical device being made. For example, if the medical device being made includes an elongate member, such as a rod, strut, or other elongate member, a tubular marker stock member may be selected to allow a marker formed from the marker stock member to be disposed circumferentially about the rod member or other elongate member of the medical device. Similarly, if the medical device being made includes a passageway in a wall member, for example, a rod marker stock member may be selected to allow a marker formed from the marker stock member to be disposed in the passageway of the medical device. Examples of suitable marker stock member types and dimensions includes those described above for the first example method of making a medical device.

The step 1106 of separating a portion of the marker stock member from the remainder of the marker stock member can be accomplished by cutting a portion of the marker stock member from the remainder of the marker stock member, such as by laser cutting or other suitable technique. For this step in this example method, the separating can be performed in a manner that contributes work to the stainless steel of the portion of the marker stock member being separated from the remainder of the marker stock member. Laser cutting and similar techniques are considered suitable for this reason; crimping, folding, and other cold working techniques are also considered suitable for the same reason. Importantly, though, if a technique selected for this step contributes work to the stainless steel of the portion of the marker stock member being separated from the remainder of the marker stock member, the portion of the marker stock member being separated from the remainder of the marker stock member should have an ultimate tensile strength that is less than the identified final ultimate tensile strength to allow the subsequent step 1110 to contribute work to the marker toward achieving the final ultimate tensile strength.

In the step 1108 of identifying a desired final ultimate tensile strength for the marker, the final ultimate tensile strength selected need only be greater than the starting ultimate tensile strength of the marker stock member and be achievable by the cold working performed on the marker in step 1110. Also, as described herein, it is considered critical that the final ultimate tensile strength selected be between about 100 KSI and about 225 KSI. The inventor has determined that a final ultimate tensile strength between about 150 KSI and about 200 KSI can be advantageous. Furthermore, the inventor has determined that a final ultimate tensile strength between about 170 KSI and about 200 KSI can be advantageous. Furthermore, the inventor has determined that a final ultimate tensile strength between about 172 KSI and about 197 KSI can be advantageous. Furthermore, the inventor has determined that a final ultimate tensile strength between about 187 KSI and about 191 KSI can be advantageous. Furthermore, the inventor has determined that a final ultimate tensile strength of about 189 KSI can be advantageous.

The step 1110 of cold working the marker until the marker has a marker ultimate tensile strength that is substantially the same as the final ultimate tensile strength identified in step 1108 can be accomplished using any suitable cold working technique. Examples of suitable cold working techniques includes crimping, swaging, hammering, folding, bending, forming, rolling, knurling, cold forging, sizing, riveting, stacking, coining, peening, blanking, dinking, deep drawing, stretching, and dimpling. No matter the technique chosen for step 1110 in a method according to a particular embodiment, it is considered important that the step 1110 of cold working the marker be performed such that the stainless steel of the marker, once step 1110 is completed, has an ultimate tensile strength of between about 100 KSI and about 225 KSI. Furthermore, the inventor has determined that performing this step 1110 until the stainless steel of the marker has an ultimate tensile strength of between about 150 KSI and about 200 KSI is advantageous. Furthermore, the inventor has determined that performing this step 1110 until the stainless steel of the marker has an ultimate tensile strength of between about 170 KSI and about 200 KSI is advantageous. Furthermore, the inventor has determined that performing this step 1110 until the stainless steel of the marker has an ultimate tensile strength of between about 172 KSI and about 197 KSI is advantageous. Furthermore, the inventor has determined that performing this step 1110 until the stainless steel of the marker has an ultimate tensile strength of between about 187 KSI and about 191 KSI is advantageous. Furthermore, the inventor has determined that performing this step 1110 until the stainless steel of the marker has an ultimate tensile strength of about 189 KSI is advantageous.

The step 1112 of attaching the marker to the body member in a manner that does not contribute substantial work to the stainless steel of the marker can be accomplished using any suitable attachment technique that does not further cold work the marker. Examples of suitable techniques include adhering the marker to the body member of the medical device precursor with an adhesive, welding the marker to the body member, bonding, reflowing a polymer around the marker, potting, and other similar techniques.

Figure 8:
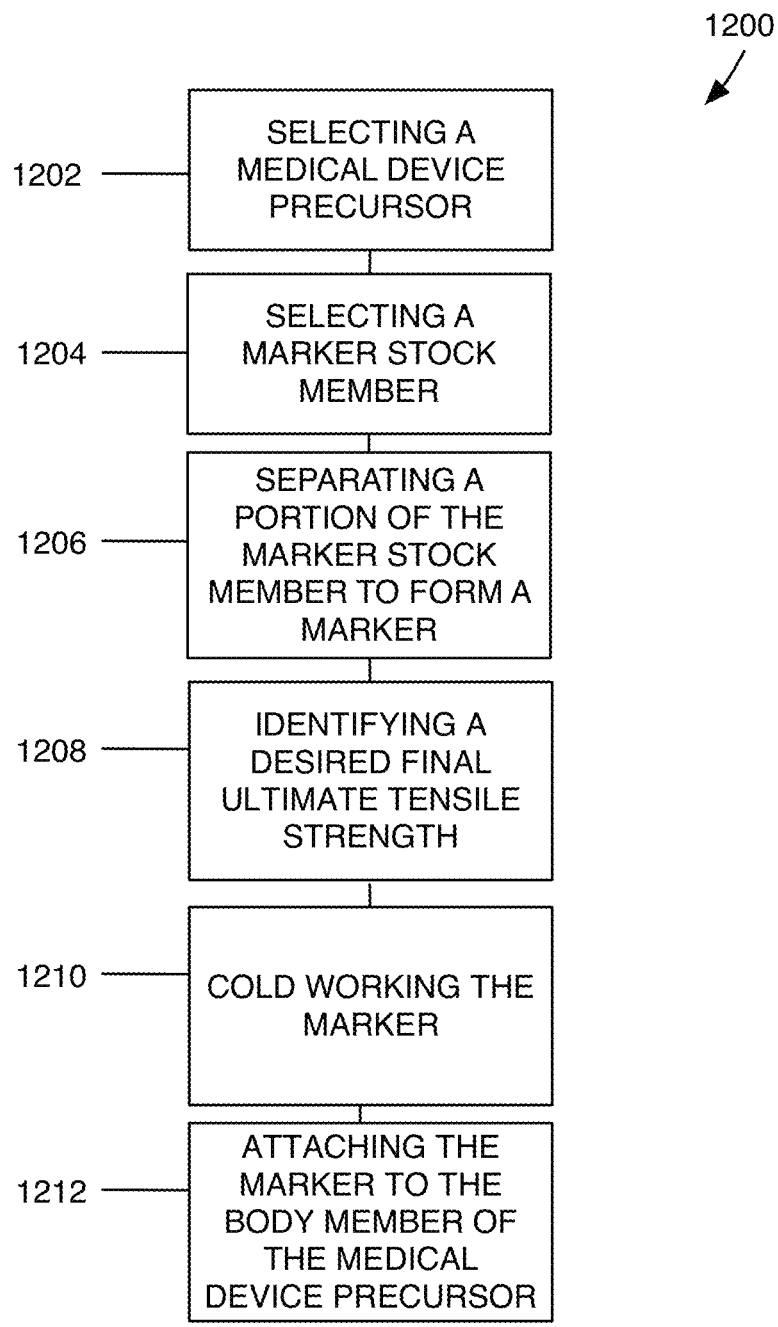
FIG. 8 is a schematic illustration of another example method of making a medical device.

FIG. 8 is a schematic illustration of another example method 1200 of making a medical device. An initial step 1202 comprises selecting a medical device precursor having a body member having proximal and distal ends. Another step 1204 comprises selecting a marker stock member formed of stainless steel having a starting ultimate tensile strength. Another step 1206 comprises separating a portion of the marker stock member from the remainder of the marker stock member to form a marker. Another step 1208 comprises identifying a desired final ultimate tensile strength for the marker. Another step 1210 comprises cold working the marker until the marker has a marker ultimate tensile strength that is greater than the starting ultimate tensile strength but less than the final ultimate tensile strength identified in step 1208. Another step 1212 comprises attaching the marker to the body member in a manner that contributes work to the stainless steel of the marker such that once the attaching step 1212 is completed the ultimate tensile strength of the marker is substantially the ultimate tensile strength identified in step 1208.

The step 1202 of selecting a medical device precursor can be accomplished by identifying a medical device or a medical device for which it is desirable to attach a marker for purposes of using the medical device with magnetic resonance imaging. The medical device can be any suitable medical device, or a precursor to such a medical device. Examples of suitable medical devices include guidewires, catheters, needles, sheaths, snares, and other suitable interventional medical devices. Also, implantable medical devices, such as stents, frames, valves, filters, occluders, and other devices can be selected in this step as well.

The step 1204 of selecting a marker stock member can be accomplished by identifying a marker stock member of stainless steel having dimensions suitable for use, with modification in subsequent steps, as a marker for the medical device identified in step 1202. For this step in this example method, the stainless steel can be annealed, as the cold working completed in subsequent steps 1210 and 1212 contributes the work needed to produce the desired visual artifact. Importantly, though, for this step in this example method, the stainless steel can be non-annealed as long as the stainless steel has an ultimate tensile strength that allows for the input of work via cold working to achieve the desired final ultimate tensile strength in subsequent steps. The marker stock member selected has a starting ultimate tensile strength. Examples of suitable types of marker stock members including rods, ribbons, bars, and tubular members. The specific type of marker stock member selected in a particular method of making a medical device will depend on various considerations, include the nature of the medical device being made. For example, if the medical device being made includes an elongate member, such as a rod, strut, or other elongate member, a tubular marker stock member may be selected to allow a marker formed from the marker stock member to be disposed circumferentially about the rod member or other elongate member of the medical device. Similarly, if the medical device being made includes a passageway in a wall member, for example, a rod marker stock member may be selected to allow a marker formed from the marker stock member to be disposed in the passageway of the medical device. Examples of suitable marker stock member types and dimensions includes those described above for the first example method of making a medical device.

The step 1206 of separating a portion of the marker stock member from the remainder of the marker stock member can be accomplished by cutting a portion of the marker stock member from the remainder of the marker stock member, such as by laser cutting or other suitable technique. For this step in this example method, the separating can be performed in a manner that contributes work to the stainless steel of the portion of the marker stock member being separated from the remainder of the marker stock member. Laser cutting and similar techniques are considered suitable for this reason; crimping, folding, and other cold working techniques are also considered suitable for the same reason. Importantly, though, if a technique selected for this step contributes work to the stainless steel of the portion of the marker stock member being separated from the remainder of the marker stock member, the portion of the marker stock member being separated from the remainder of the marker stock member should have an ultimate tensile strength that is less than the identified final ultimate tensile strength to allow the subsequent steps 1210 and 1212 to contribute work to the marker toward achieving the final ultimate tensile strength.

In the step 1208 of identifying a desired final ultimate tensile strength for the marker, the final ultimate tensile strength selected need only be greater than the starting ultimate tensile strength of the marker stock member and be achievable by the cold working performed on the marker in steps 1210 and 1212. Also, as described herein, it is considered critical that the final ultimate tensile strength selected be between about 100 KSI and about 225 KSI. The inventor has determined that a final ultimate tensile strength between about 150 KSI and about 200 KSI can be advantageous. Furthermore, the inventor has determined that a final ultimate tensile strength between about 170 KSI and about 200 KSI can be advantageous. Furthermore, the inventor has determined that a final ultimate tensile strength between about 172 KSI and about 197 KSI can be advantageous. Furthermore, the inventor has determined that a final ultimate tensile strength between about 187 KSI and about 191 KSI can be advantageous. Furthermore, the inventor has determined that a final ultimate tensile strength of about 189 KSI can be advantageous.

The step 1210 of cold working the marker until the marker has a marker ultimate tensile strength that is greater than the starting ultimate tensile strength of the marker stock member but less than the final ultimate tensile strength identified in step 1208 can be accomplished using any suitable cold working technique. Examples of suitable cold working techniques includes crimping, swaging, hammering, folding, bending, forming, rolling, knurling, cold forging, sizing, riveting, stacking, coining, peening, blanking, dinking, deep drawing, stretching, and dimpling. No matter the technique chosen for step 1210 in a method according to a particular embodiment, it is considered important that the step 1210 of cold working the marker be performed such that the stainless steel of the marker, once step 1210 is completed, has an ultimate tensile strength that is less than the final ultimate tensile strength identified in step 1208. While not critical considering the effect of step 1212 on the ultimate tensile strength of the stainless steel of the marker, the step 1210 can be performed until the stainless steel of the marker has an ultimate tensile strength of between about 100 KSI and about 225 KSI. Furthermore, the inventor has determined that performing this step 1210 until the stainless steel of the marker has an ultimate tensile strength of between about 150 KSI and about 200 KSI is advantageous. Furthermore, the inventor has determined that performing this step 1210 until the stainless steel of the marker has an ultimate tensile strength of between about 170 KSI and about 200 KSI is advantageous. Furthermore, the inventor has determined that performing this step 1210 until the stainless steel of the marker has an ultimate tensile strength of between about 172 KSI and about 197 KSI is advantageous. Furthermore, the inventor has determined that performing this step 1210 until the stainless steel of the marker has an ultimate tensile strength of between about 187 KSI and about 191 KSI is advantageous. Furthermore, the inventor has determined that performing this step 1210 until the stainless steel of the marker has an ultimate tensile strength of between about 187 KSI and about 191 KSI is advantageous, particularly in methods in which the final ultimate tensile strength identified in step 1208 is about 189 KSI.

The step 1212 of attaching the marker to the body member in a manner that contributes work to the stainless steel of the marker can be accomplished in any suitable manner that cold works the marker, formed in the separating step 1206, such that the stainless steel in the marker, once the step 1212 of attaching is completed, has an ultimate tensile strength that is substantially the ultimate tensile strength identified in step 1208. Examples of suitable cold working techniques include crimping, swaging, and hammering. The technique chosen for a particular method of making a medical device will depend on various considerations, including the nature of the medical device being made and the nature of the marker formed in step 1206. For example, if the marker formed in step 1206 is a tubular member defining a lumen and the medical device being made includes an elongate member, such as a rod, strut, or other elongate member, the marker can be attached to the body member of the medical device precursor by disposing the marker circumferentially about the elongate member of the medical device and crimping the marker onto the elongate member. Also, if the marker formed in step 1206 is a rod, plug, or other non-lumen defining member and the medical device being made includes a wall member or other portion defining a passageway, the marker can be attached to the body member by forcing the marker into the passageway by pushing, hammering, or otherwise forcing the marker into the passageway.

No matter the technique chosen for step 1212 in a method according to a particular embodiment, it is considered important that the step 1212 of attaching the marker to the body member be performed such that the stainless steel of the marker, once step 1212 is completed, has an ultimate tensile strength of between about 172 KSI and about 197 KSI. The inventor has determined that performing this step 1212 until the stainless steel of the marker has an ultimate tensile strength of between about 187 KSI and about 191 KSI is advantageous. Furthermore, the inventor has determined that performing this step 1212 until the stainless steel of the marker has an ultimate tensile strength of about 189 KSI is advantageous.

The extent of work performed on the stainless steel of the marker in step 1212 will depend on the extent of work performed on the stainless steel of the marker in step 1210, and the final ultimate tensile strength identified in step 1208. The total work performed on the stainless steel of the marker in both steps 1210 and 1212 will depend on the ultimate tensile strength of the marker stock member selected in step 1204 and the final ultimate tensile strength identified in step 1208. In methods according to particular embodiment in which a marker stock member comprising annealed stainless steel is selected, the inventor has determined that it is advantageous to perform the majority of the cold working required to achieve the final ultimate tensile strength in step 1210, leaving a minority of the cold working required to be completed in step 1212. For example, if the marker stock member selected in step 1204 comprises annealed 304 stainless steel having an ultimate tensile strength of about 75 KSI, it is considered advantageous to perform step 1210 until the stainless steel of the marker has an ultimate tensile strength of at least 129 KSI. Furthermore, it is considered advantageous to perform step 1210 until the stainless steel of the marker has an ultimate tensile strength of at least 150 KSI. Furthermore, it is considered advantageous to perform step 1210 until the stainless steel of the marker has an ultimate tensile strength of at least 170 KSI. Furthermore, in a method in which the final ultimate tensile strength identified in step 1208 is between about 187 KSI and about 191 KSI, it is considered advantageous to perform step 1210 until the stainless steel of the marker has an ultimate tensile strength of at least 180 KSI. For these same methods, it is also considered advantageous to perform step 1210 until the stainless steel of the marker has an ultimate tensile strength of at least 185 KSI.

Figure 9:
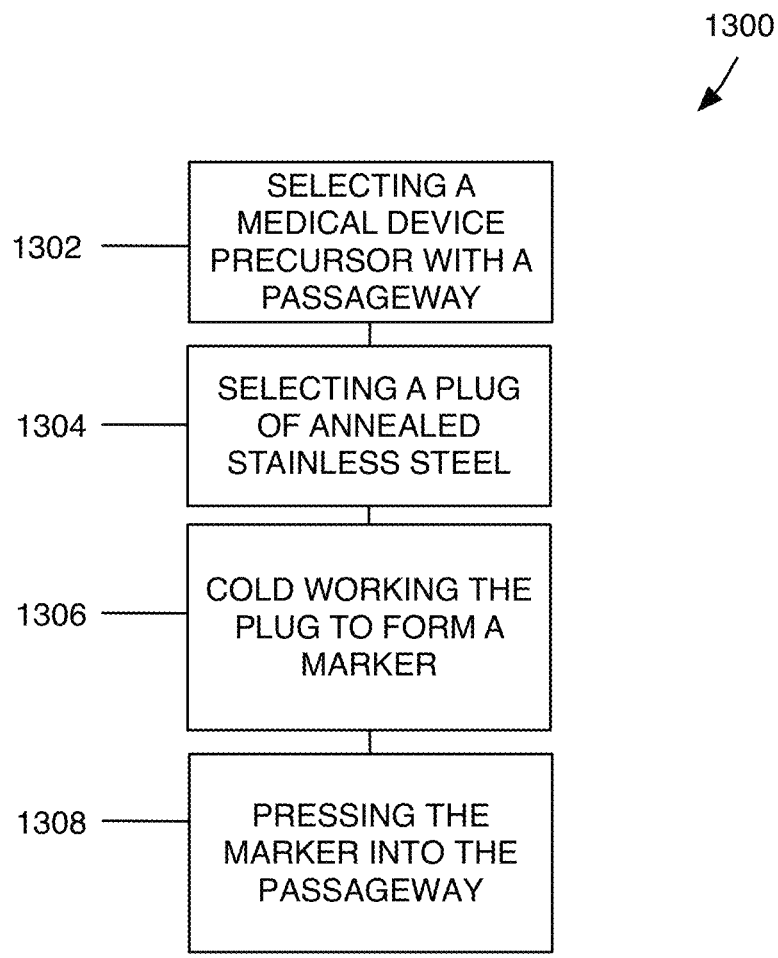
FIG. 9 is a schematic illustration of another example method of making a medical device.

FIG. 9 is a schematic illustration of another example method 1300 of making a medical device. An initial step 1302 comprises selecting a medical device precursor having a body member having proximal and distal ends, a first surface, a second surface, a thickness, and defining a passageway extending from the first surface toward the second surface. Another step 1304 comprises selecting a plug of annealed stainless steel. Another step 1306 comprises cold working the plug to form a marker. Another step 1308 comprises pressing the marker into the passageway. An optional additional step includes fixedly securing the marker to the body member, such as by laser welding the marker to the body member. Another optional additional step includes grinding a surface of the marker to make it flush with the first surface of the body member. Another optional additional step includes grinding another surface of the marker to make it flush with the second surface of the body member. Another optional additional step includes polishing one or more surfaces of the marker.

To provide access to the passageway, a medical device precursor in which the first surface defines a first opening to the passageway should be selected. In these methods, the passageway can extend only partially through the thickness. In methods according to some embodiments, a medical device precursor in which the second surface defines a second opening to the passageway can be selected. In these methods, the passageway extends through the entire thickness, from the first surface to the second surface.

Figure 10:
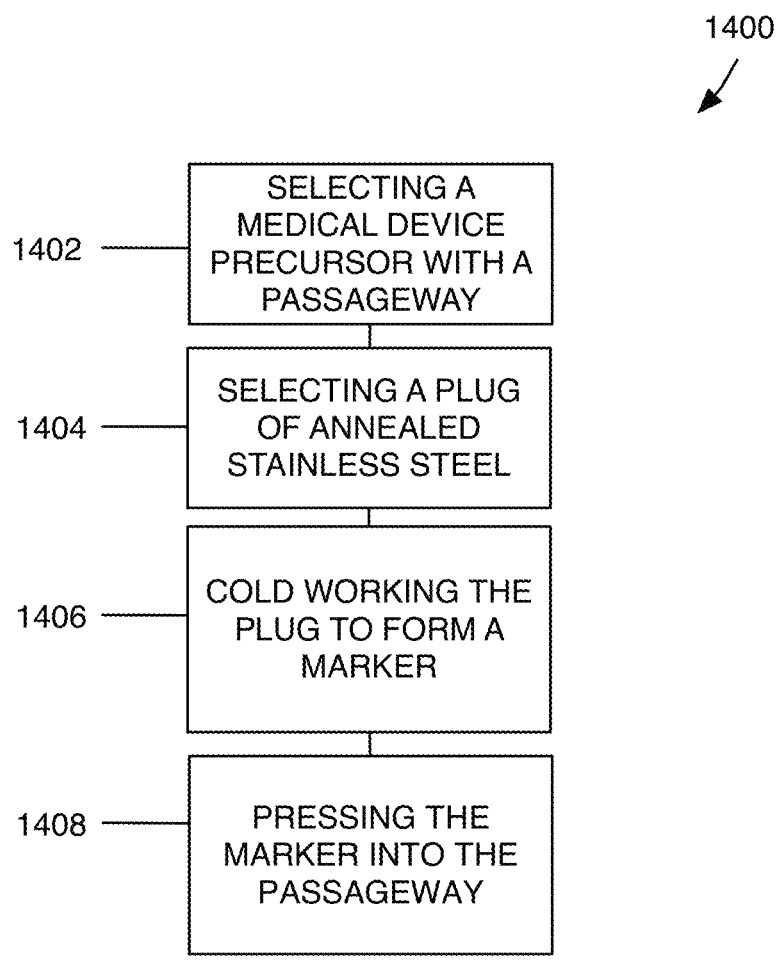
FIG. 10 is a schematic illustration of another example method of making a medical device.

FIG. 10 is a schematic illustration of another example method 1400 of making a medical device. An initial step 1402 comprises selecting a medical device precursor having a body member having proximal and distal ends, a first surface, a second surface, a thickness, and defining a passageway extending from the first surface toward the second surface. Another step 1404 comprises selecting a plug of annealed stainless steel. Another step 1406 comprises cold working the plug to form a marker having an ultimate tensile strength between about 172 KSI and about 197 KSI. Another step 1408 comprises pressing the marker into the passageway.

Figure 11:
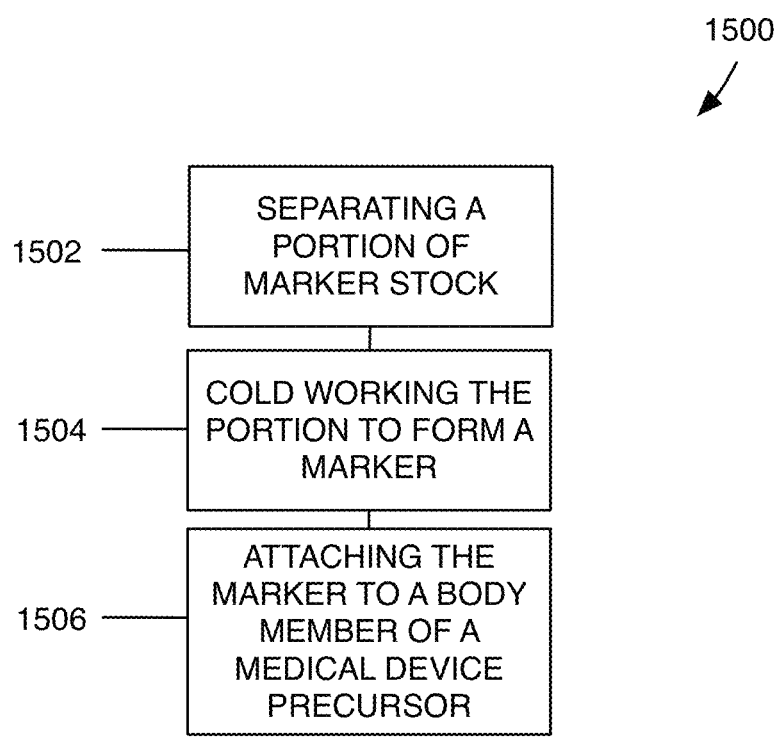
FIG. 11 is a schematic illustration of another example method of making a medical device.

FIG. 11 is a schematic illustration of another example method 1500 of making a medical device. An initial step 1502 comprises separating a portion of marker stock from a marker stock member comprising annealed stainless steel. Another step 1504 comprises cold working the portion or marker stock to form a marker having an ultimate tensile strength between about 172 KSI and about 197 KSI. Another step 1506 comprises attaching the marker to a body member of a medical device precursor to form said medical device.

Figure 12:
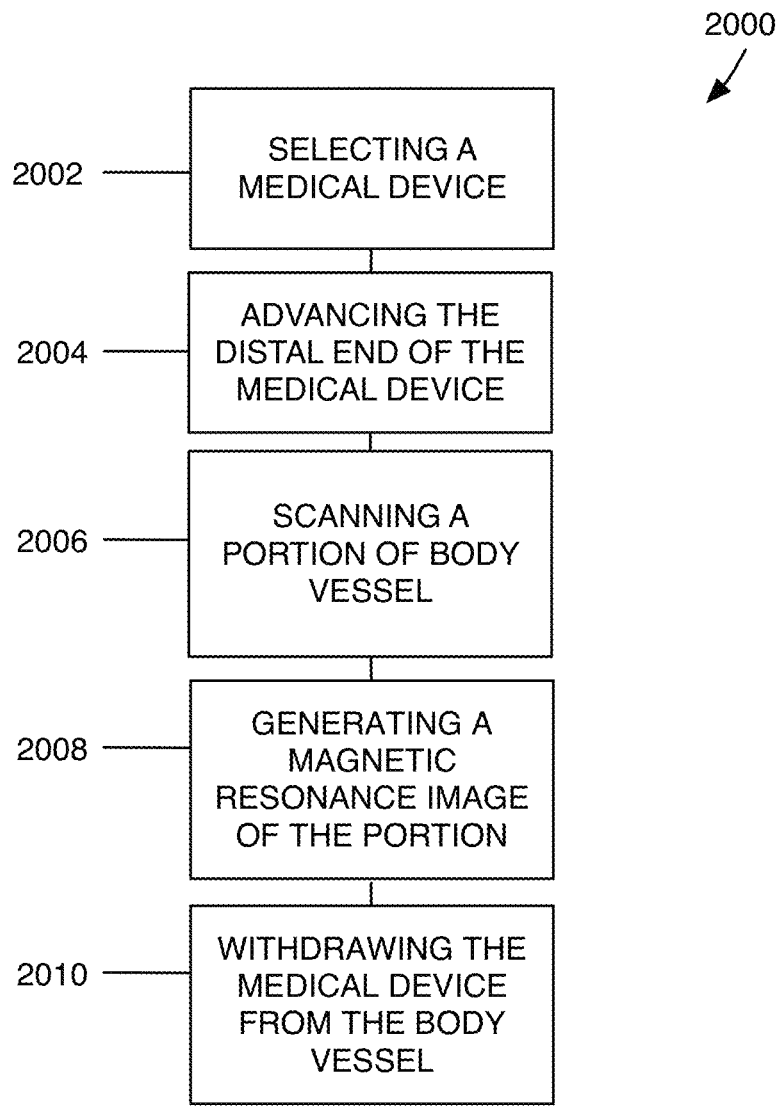
FIG. 12 is a schematic illustration of an example imaging method.

FIG. 12 is a schematic illustration of an example imaging method 2000. An initial step 2002 comprises selecting a medical device having a body member having proximal and distal ends and comprising a marker attached to the body member. The marker is formed of work hardened stainless steel. Another step 2004 comprises advancing the distal end of the medical device to a first location within a body vessel of a patient and until the marker is disposed at a second location within the body vessel. Another step 2006 comprises scanning a portion of the body vessel that includes the first and second locations within the body vessel using a magnetic resonance scanner. Another step 2008 comprises obtaining a magnetic resonance image of the portion of the body vessel such that the image includes an artifact indicative of the presence of the marker within the portion of the body vessel. For this step 2008, a single still image can be obtained. Also, and optionally, this step 2008 can be repeated any desired number of times to obtain multiple magnetic resonance images that can be grouped as a cine to show motion. Another step 2010 comprises withdrawing the medical device from the body vessel.

In the step 2002 of selecting a medical device, it is considered critical that the stainless steel of the marker have an ultimate tensile strength between about 100 KSI and about 225 KSI. The inventor has determined that an ultimate tensile strength between about 150 KSI and about 200 KSI can be advantageous. Furthermore, the inventor has determined that an ultimate tensile strength between about 170 KSI and about 200 KSI can be advantageous. Furthermore, the inventor has determined that an ultimate tensile strength between about 172 KSI and about 197 KSI can be advantageous. Furthermore, the inventor has determined that an ultimate tensile strength between about 187 KSI and about 191 KSI can be advantageous. Furthermore, the inventor has determined that an ultimate tensile strength of about 189 KSI can be advantageous.

Figure 13:
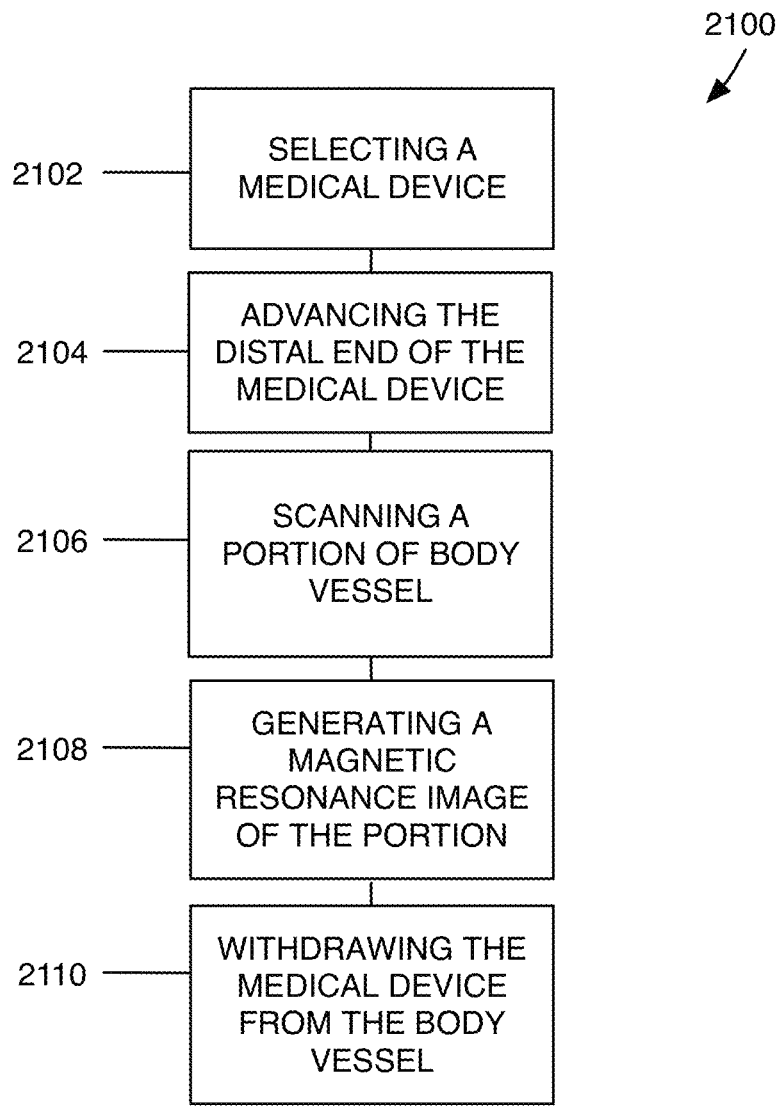
FIG. 13 is a schematic illustration of another example imaging method.

FIG. 13 is a schematic illustration of another example imaging method 2100. An initial step 2102 comprises selecting a medical device having a body member having proximal and distal ends and comprising a stainless steel marker attached to the body member. The marker has an ultimate tensile strength of between about 172 KSI and about 197 KSI. Another step 2104 comprises advancing the distal end of the medical device to a first location within a body vessel of a patient and until the marker is disposed at a second location within the body vessel. Another step 2106 comprises scanning a portion of the body vessel that includes the first and second locations within the body vessel using a magnetic resonance scanner. Another step 2108 comprises obtaining a magnetic resonance image of the portion of the body vessel such that the image includes an artifact indicative of the presence of the marker within the portion of the body vessel. Another step 2110 comprises withdrawing the medical device from the body vessel.

Figure 14:
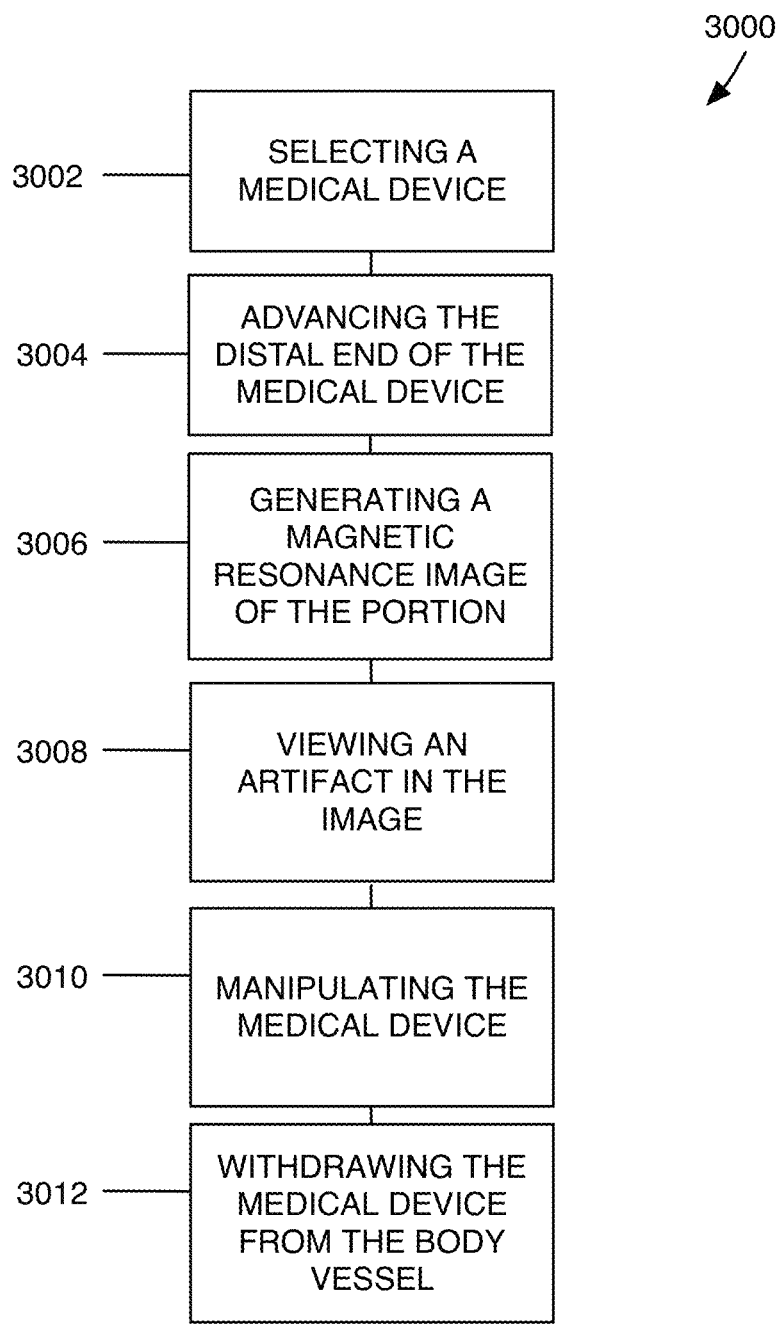
FIG. 14 is a schematic illustration of an example method of performing an interventional medical treatment.

FIG. 14 is a schematic illustration of an example method 3000 of performing an interventional medical treatment. An initial step 3002 comprises selecting a medical device having a body member having proximal and distal ends and comprising a marker attached to the body member. The marker is formed of work hardened stainless steel. Another step 3004 comprises advancing the distal end of the medical device to a first location within a body vessel of a patient and until the marker is disposed at a second location within the body vessel. Another step 3006 comprises obtaining a magnetic resonance image of a portion of the body vessel that includes the second location while the marker is disposed at the second location within the body vessel. Another step 3008 comprises viewing an artifact in the image generated by the presence of the marker during the step 3006 of obtaining a magnetic resonance image of the portion of the body vessel. Another step 3010 comprises manipulating the medical device based on the location of the artifact relative to the body vessel. Another step 3012 comprises withdrawing the medical device from the body vessel.

In the step 3002 of selecting a medical device, it is considered critical that the stainless steel of the marker have an ultimate tensile strength between about 100 KSI and about 225 KSI. The inventor has determined that an ultimate tensile strength between about 150 KSI and about 200 KSI can be advantageous. Furthermore, the inventor has determined that an ultimate tensile strength between about 170 KSI and about 200 KSI can be advantageous. Furthermore, the inventor has determined that an ultimate tensile strength between about 172 KSI and about 197 KSI can be advantageous. Furthermore, the inventor has determined that an ultimate tensile strength between about 187 KSI and about 191 KSI can be advantageous. Furthermore, the inventor has determined that an ultimate tensile strength of about 189 KSI can be advantageous.

The step 3010 of manipulating the medical device is performed in a manner that achieves, or that contributes to the achievement of, a desired clinical outcome of the method 3000 of performing an interventional medical treatment. As such, the nature of the step 3010 of manipulating the medical device will depend on the nature of the medical device and the desired clinical outcome. Examples of suitable actions that can be performed for this step include, but are not limited to, axially advancing the medical device within the body vessel, rotating the medical device within the body vessel, radially expanding the medical device within the body vessel, and axially withdrawing a portion of the medical device to allow another portion of the medical device, or a second medical device associated with the medical device, to radially expand within the body vessel.

Figure 15:
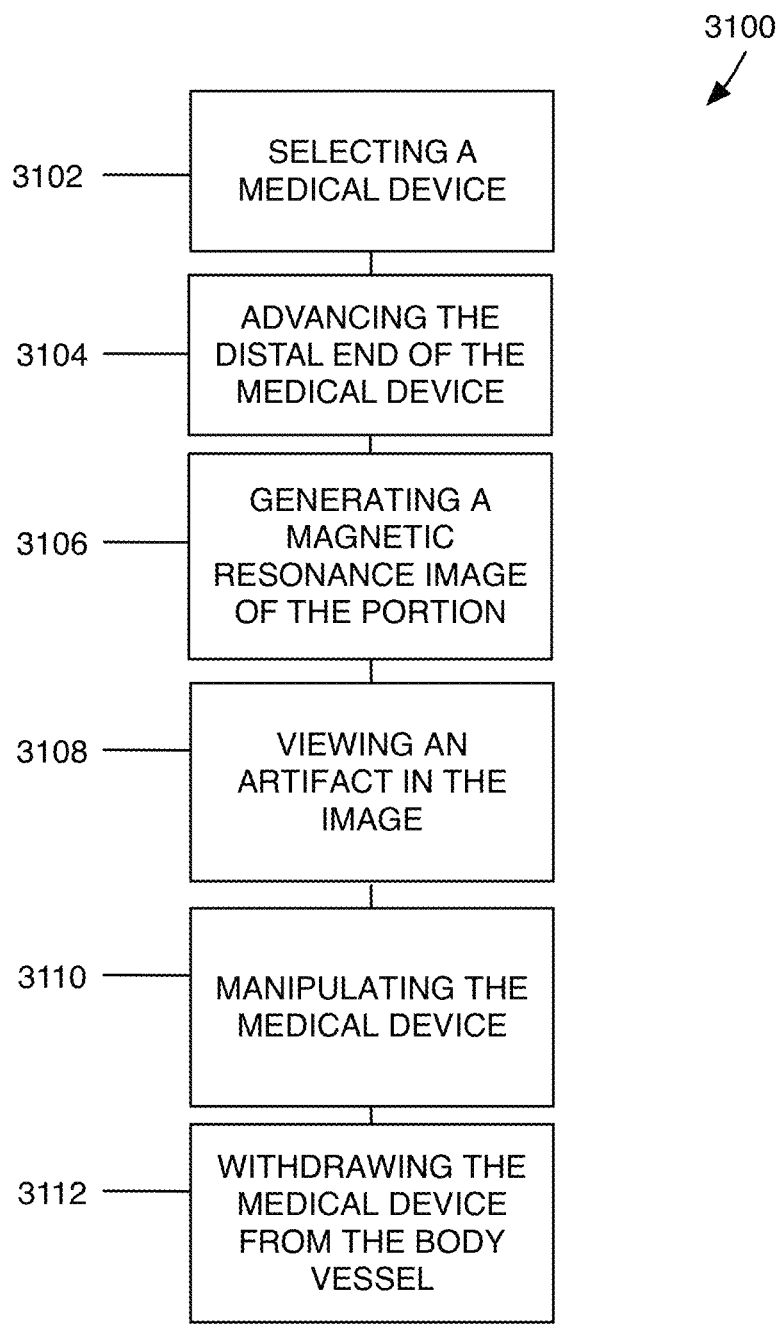
FIG. 15 is a schematic illustration of another example method of performing an interventional medical treatment.

FIG. 15 is a schematic illustration of another example method 3100 of performing an interventional medical treatment. An initial step 3102 comprises selecting a medical device having a body member having proximal and distal ends and comprising a stainless steel marker attached to the body member. The marker has an ultimate tensile strength of between about 172 KSI and about 197 KSI. Another step 3104 comprises advancing the distal end of the medical device to a first location within a body vessel of a patient and until the marker is disposed at a second location within the body vessel. Another step 3106 comprises obtaining a magnetic resonance image of a portion of the body vessel that includes the second location while the marker is disposed at the second location within the body vessel. Another step 3108 comprises viewing an artifact in the image generated by the presence of the marker during the step 3106 of obtaining a magnetic resonance image of the portion of the body vessel. Another step 3110 comprises manipulating the medical device based on the location of the artifact relative to the body vessel. Another step 3112 comprises withdrawing the medical device from the body vessel.

The step 3110 of manipulating the medical device is performed in a manner that achieves, or that contributes to the achievement of, a desired clinical outcome of the method 3100 of performing an interventional medical treatment. As such, the nature of the step 3110 of manipulating the medical device will depend on the nature of the medical device and the desired clinical outcome. Examples of suitable actions that can be performed for this step include, but are not limited to, axially advancing the medical device within the body vessel, rotating the medical device within the body vessel, radially expanding the medical device within the body vessel, and axially withdrawing a portion of the medical device to allow another portion of the medical device, or a second medical device associated with the medical device, to radially expand within the body vessel.

Figure 16:
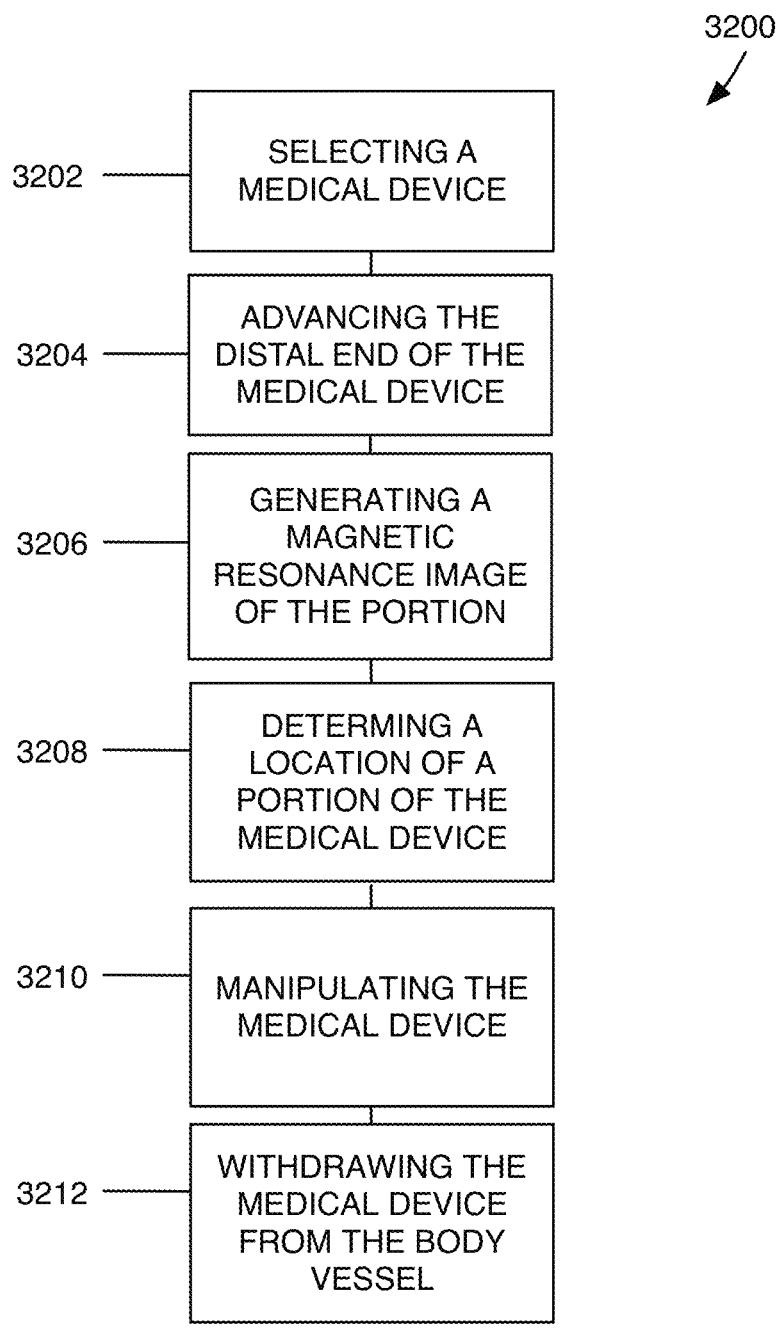
FIG. 16 is a schematic illustration of another example method of performing an interventional medical treatment.

FIG. 16 is a schematic illustration of another example method 3200 of performing an interventional medical treatment. An initial step 3202 comprises selecting a medical device having a body member having proximal and distal ends and comprising a marker attached to the body member. The marker is formed of work hardened stainless steel. Another step 3204 comprises advancing the distal end of the medical device to a first location within a body vessel of a patient and until the marker is disposed at a second location within the body vessel. Another step 3206 comprises obtaining a magnetic resonance image of a portion of the body vessel that includes the second location while the marker is disposed at the second location within the body vessel. Another step 3208 comprises determining a location of a portion of the medical device within the body vessel based at least partially on an artifact in the image generated by the presence of the marker during the step 3206 of obtaining a magnetic resonance image of the portion of the body vessel. Another step 3210 comprises manipulating the medical device within the body vessel. Another step 3212 comprises withdrawing the medical device from the body vessel.

In the step 3202 of selecting a medical device, it is considered critical that the stainless steel of the marker have an ultimate tensile strength between about 100 KSI and about 225 KSI. The inventor has determined that an ultimate tensile strength between about 150 KSI and about 200 KSI can be advantageous. Furthermore, the inventor has determined that an ultimate tensile strength between about 170 KSI and about 200 KSI can be advantageous. Furthermore, the inventor has determined that an ultimate tensile strength between about 172 KSI and about 197 KSI can be advantageous. Furthermore, the inventor has determined that an ultimate tensile strength between about 187 KSI and about 191 KSI can be advantageous. Furthermore, the inventor has determined that an ultimate tensile strength of about 189 KSI can be advantageous.

The step 3210 of manipulating the medical device is performed in a manner that achieves, or that contributes to the achievement of, a desired clinical outcome of the method 3200 of performing an interventional medical treatment. As such, the nature of the step 3210 of manipulating the medical device will depend on the nature of the medical device and the desired clinical outcome. Examples of suitable actions that can be performed for this step include, but are not limited to, axially advancing the medical device within the body vessel, rotating the medical device within the body vessel, radially expanding the medical device within the body vessel, and axially withdrawing a portion of the medical device to allow another portion of the medical device, or a second medical device associated with the medical device, to radially expand within the body vessel.

Figure 17:
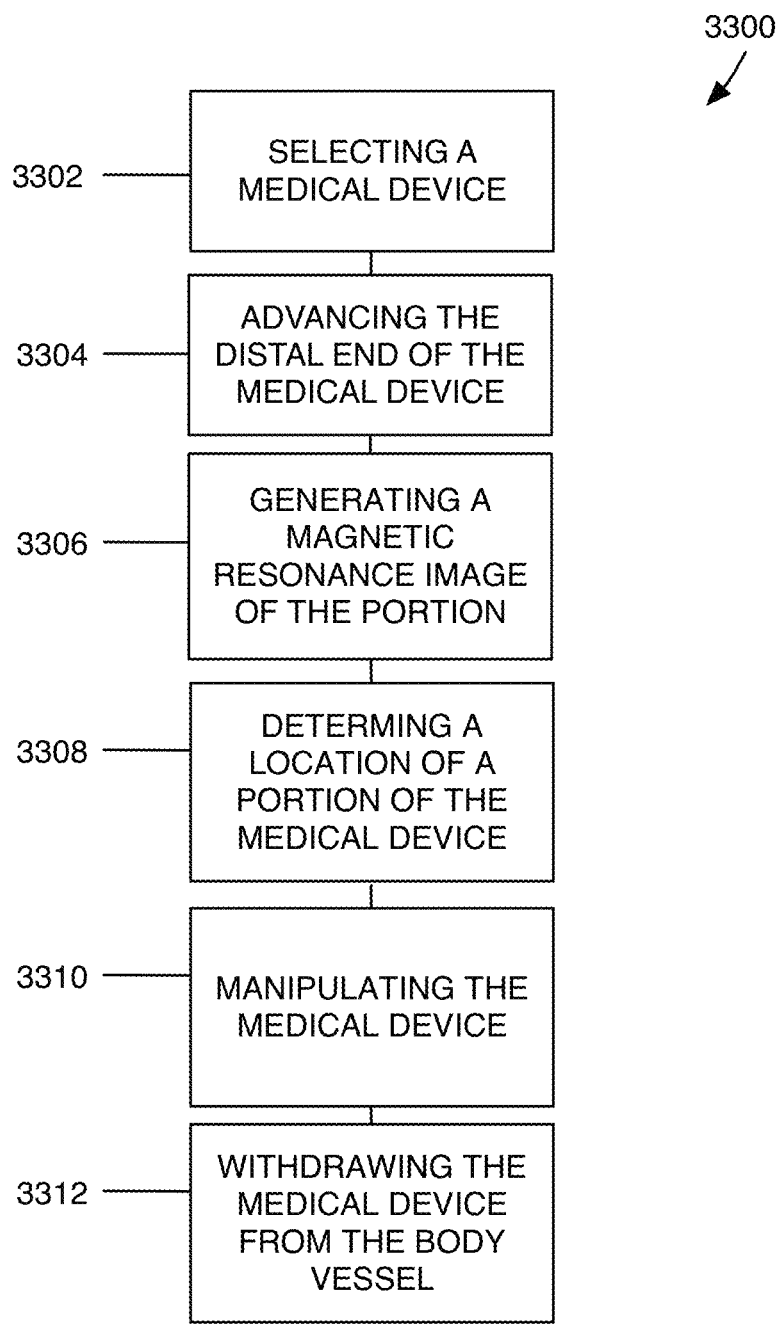
FIG. 17 is a schematic illustration of another example method of performing an interventional medical treatment.

FIG. 17 is a schematic illustration of another example method 3300 of performing an interventional medical treatment. An initial step 3302 comprises selecting a medical device having a body member having proximal and distal ends and comprising a stainless steel marker attached to the body member. The marker has an ultimate tensile strength of between about 172 KSI and about 197 KSI. Another step 3304 comprises advancing the distal end of the medical device to a first location within a body vessel of a patient and until the marker is disposed at a second location within the body vessel. Another step 3306 comprises obtaining a magnetic resonance image of a portion of the body vessel that includes the second location while the marker is disposed at the second location within the body vessel. Another step 3308 comprises determining a location of a portion of the medical device within the body vessel based at least partially on an artifact in the image generated by the presence of the marker during the step 3306 of obtaining a magnetic resonance image of the portion of the body vessel. Another step 3310 comprises manipulating the medical device within the body vessel. Another step 3312 comprises withdrawing the medical device from the body vessel.

The step 3310 of manipulating the medical device is performed in a manner that achieves, or that contributes to the achievement of, a desired clinical outcome of the method 3300 of performing an interventional medical treatment. As such, the nature of the step 3310 of manipulating the medical device will depend on the nature of the medical device and the desired clinical outcome. Examples of suitable actions that can be performed for this step include, but are not limited to, axially advancing the medical device within the body vessel, rotating the medical device within the body vessel, radially expanding the medical device within the body vessel, and axially withdrawing a portion of the medical device to allow another portion of the medical device, or a second medical device associated with the medical device, to radially expand within the body vessel.

In all embodiments, any suitable stainless steel can be used for the stainless steel of a required marker or marker stock. The inventor has determined that austenitic stainless steel is particularly well-suited for use in the markers and marker stock of the various medical devices and methods described herein. Furthermore, the inventor has determined that stainless steel comprising an austenitic chromium-nickel alloy is particularly well-suited for use in the markers and marker stock of the various medical devices and methods described herein. Furthermore, the inventor has determined that stainless steel comprising a stainless steel in the SAE International 300 Series of stainless steels is particularly well-suited for use in the markers and marker stock of the various medical devices and methods described herein. In particular embodiments, the stainless steel used in a marker or marker stock comprises SAE Type 301 stainless steel, SAE Type 302 stainless steel, SAE Type 303 stainless steel, SAE Type 304 stainless steel, SAE Type 304L stainless steel, SAE Type 304LN stainless steel, SAE Type 308 stainless steel, SAE Type 309 stainless steel, SAE Type 310 stainless steel, SAE Type 310S stainless steel, SAE Type 316 stainless steel, SAE Type 316L stainless steel, SAE Type 316Ti stainless steel, or SAE Type 321 stainless steel. The inventor has determined that SAE Type 304 stainless steel is particularly advantageous for use in a marker or marker stock of the various medical devices and methods described herein. Other stainless steels, such as a ferritic stainless steel, can also be used for the stainless steel of a required marker or marker stock.

EXPERIMENTAL EXAMPLES

Example 1—Ultimate Tensile Strength and Artifact Size

Methods: Seven marker stock members, each comprising a stainless steel tubular member with known dimensions and ultimate tensile strength were laser cut into 1 mm length tubular markers. Each marker was then attached to a nitinol rod by circumferentially disposing the marker over the rod. The rod and marker assembly was then placed in an ASTM imaging phantom. Samples were scanned at 1.5 T Siemens Aera Scanner with the following two sequences:

GRE—Flip angle: 25 Slice thickness 8 mm, TR/TE:100/10 ms (research scan)

Trufi—Flip angle: 70 Slice thickness 8 mm, TR/TE:3.4/1.6 ms (clinical)

MR images were acquired in all three imaging planes, Sagittal, Coronal and Transverse. Image artifact size was calculated for each plane.

Results

Stainless steel markers' dimensions, weight and image artifact size are reported in Table I below.

TABLE I

Effects of Cold Working and Mass on MRI Image Artifact Size

| # | Ultimate Tensile Strength (UTS) | Weight (mg) | Dimensions (OD, ID, WT, length) | Imaging plane | Artifact size (sq. cm) | |
|---|---|---|---|---|---|---|
| | | | | | GRE (TE 10 ms) | TRUFI (TE 1.6 ms) |
| A | 189 | 0.78 | 0.025", 0.021", 0.002, 1 mm | Sagittal | 4.2 | 3.2 |
| | | | | Coronal | 3.6 | 2.5 |
| | | | | Transverse | 3.5 | 1.6 |
| B | 175 | 0.71 | | Sagittal | 2.7 | 1.5 |
| | | | | Coronal | 2.5 | 1.7 |
| | | | | Transverse | 3.0 | 1.1 |
| C | 176 | 1.08 | 0.025", 0.019", 0.003, 1 mm | Sagittal | 2.5 | 1.2 |
| | | | | Coronal | 2.6 | 1.2 |
| | | | | Transverse | 2.3 | 0.8 |
| D | 197 | 1.06 | | Sagittal | 6.1 | 4.2 |
| | | | | Coronal | 7.0 | 5.5 |
| | | | | Transverse | 6.0 | 3.6 |
| E | 197 | 1.16 | 0.028", 0.022", 0.003, 1 mm | Sagittal | 7.7 | 5.2 |
| | | | | Coronal | 9.6 | 5.4 |
| | | | | Transverse | 6.8 | 3.1 |
| F | 172 | 1.16 | | Sagittal | 5.0 | 3.2 |
| | | | | Coronal | 5.5 | 3.6 |
| | | | | Transverse | 4.7 | 2.8 |
| G | N/A | 1.37 | 0.032", 0.026", 0.003", 1 mm | Sagittal | 5.1 | 3.4 |
| | | | | Coronal | 5.4 | 3.0 |
| | | | | Transverse | 4.7 | 2.8 |

The effect of UTS on image artifact size is clearly observed when two markers with the exact same mass but different UTS, namely, sample E (197 UTS, 1.16 mg) and sample F (172 UTS, 1.16 mg), are compared. Both have the same dimensions and weight but UTS are different. Image artifact size is significantly higher for sample E which has the highest UTS value.

Effect of mass on image artifact size can be determined by comparing sample E (197 UTS, 1.16 mg) and sample D (197 UTS, 1.06 mg). Both have the same UTS but sample E has slightly more mass that sample D, 1.16 mg vs 1.06 mg. Overall, image artifact size is bigger for sample E.

Especially when sample F (172 UTS, 1.16 mg) and sample A (189 UTS, 0.76 mg) are compared, effect of mass on image artifact is obvious. Even though sample F has a lower UTS compared to sample A, sample F has significantly higher mass and consequently bigger image artifact size than sample A.

Example 2—Ultimate Tensile Strength and Artifact Size

Methods: A set of unannealed markers were prepared by cutting 1 mm tubular markers from a marker stock member comprising cold worked 304 stainless steel tubing having an ultimate tensile strength of 176 KSI.

To prepare annealed markers, a marker stock member comprising cold worked 304 stainless steel tubing having an ultimate tensile strength of 176 KSI was first annealed in a kiln for 2 hours at 1900 degrees F. contained in an Argon filled stainless steel heat treating envelope. This produced a shiney, soft tube of the same dimensions having an ultimate tensile strength estimated at 75 KSI. 1 mm length tubular markers were then cut from the annealed marker stock member.

An unannealed marker/rod assembly was prepared by disposing markers from the set of unannealed markers on a Nitinol rod and adhering the markers to the rod.

An annealed marker/rod assembly was prepared by disposing markers from the set of annealed markers on a Nitinol rod and adhering the markers to the rod.

Figure 18A:
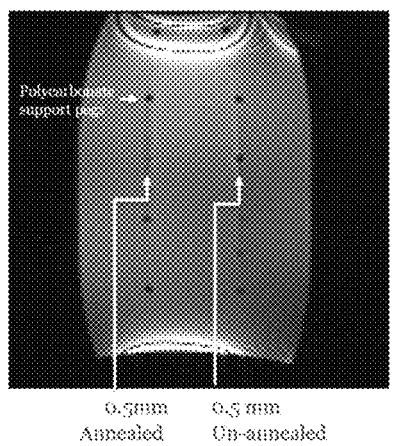
FIG. 18A is an MRI image of a first Nitinol rod onto which a set of annealed 0.5 mm stainless steel markers is attached and a second Nitinol rod onto which a set of unannealed 0.5 mm stainless steel markers is attached. Each arrow points to an artifact from one marker from the respective set of markers.
Figure 18B:
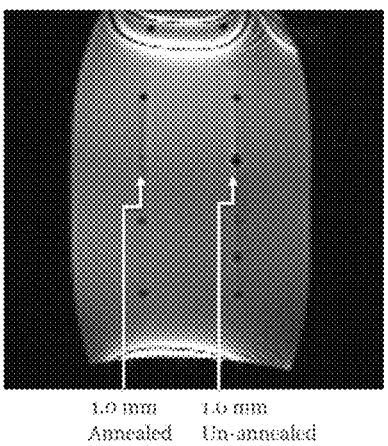
FIG. 18B is an MRI image of a first Nitinol rod onto which a set of annealed 1.0 mm stainless steel markers is attached and a second Nitinol rod onto which a set of unannealed 1.0 mm stainless steel markers is attached. Each arrow points to an artifact from one marker from the respective set of markers.
Figure 18C:
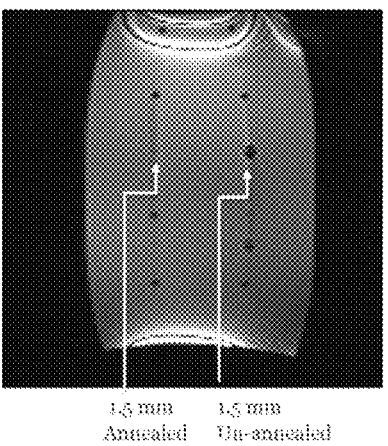
FIG. 18C is an MRI image of a first Nitinol rod onto which a set of annealed 1.5 mm stainless steel markers is attached and a second Nitinol rod onto which a set of unannealed 1.5 mm stainless steel markers is attached. Each arrow points to an artifact from one marker from the respective set of markers.

The marker/rod assemblies were then scanned side-by-side under MRI. Images from three scans, each comparing annealed and unannealed markers of the same length, with varying lengths between scans, are presented in FIGS. 18A, 18B, and 18C. The difference in artifact size between the cold worked, unannealed markers and the annealed markers is evident in each of FIGS. 18A, 18B, and 18C.

In summary, medical devices useful in interventional procedures performed under magnetic resonance imaging (MRI) are described herein. A medical device comprises a body member and a marker formed of work-hardened stainless steel attached to the body member. The stainless steel of the marker has an ultimate tensile strength of between about 100 KSI and about 225 KSI. The marker can be attached to the body member in a manner that contributes work to the stainless steel or in a manner that does not contribute work to the stainless steel. Methods of making medical devices, medical imaging methods, and methods of performing interventional medical treatment are also described herein.

While a number of imaging methods have been described herein, it will be appreciated that the method may be a non-invasive method that does not require an invasive intervention by a medical professional. For example, the method may be carried within a body lumen or passageway, such as the ear canal or a nasal passage, for example in order to place a device within such a passageway. Equally, methods may be implemented on a cadaver or artificial body parts for example for training purposes. Moreover, the skilled person will appreciate that the imaging methods described herein may not be used on the human or animal body at all, but may be used in order to view other types of devices using MRI imaging techniques, for example in an industrial setting.

Those with ordinary skill in the art will appreciate that various modifications and alternatives for the described and illustrated examples can be developed in light of the overall teachings of the disclosure. Accordingly, the particular arrangements of elements and steps disclosed are intended to be illustrative only and not limiting as to the scope of the invention, which is to be given the full breadth of the appended claims and any and all equivalents thereof.

What is claimed is:

1. A method of making a medical device useful in interventional procedures performed under magnetic resonance imaging, comprising:
   selecting a medical device precursor;
   selecting a marker stock member formed of stainless steel;
   separating a portion of the marker stock member from the remainder of the marker stock member to form a marker;
   identifying a final ultimate tensile strength of between about 100 KSI and about 225 KSI for the marker;
   cold working the marker until the marker has a marker ultimate tensile strength that is substantially the same as the final ultimate tensile strength; and
   attaching the marker to the medical device precursor to form said medical device;
   wherein the attaching is performed in a manner that does not contribute substantial work to the stainless steel of the marker such that the marker in said medical device has substantially the final ultimate tensile strength.

2. The method of claim 1, wherein the final ultimate tensile strength is between about 150 KSI and about 200 KSI.

3. The method of claim 1, wherein the final ultimate tensile strength is between about 170 KSI and about 200 KSI.

4. The method of claim 1, wherein the final ultimate tensile strength is between about 172 KSI and about 197 KSI.

5. The method of claim 1, wherein the final ultimate tensile strength is between about 187 KSI and about 191 KSI.

6. The method of claim 1, wherein the final ultimate tensile strength is about 189 KSI.

7. The method of claim 1, wherein the marker has a mass of between about 0.05 mg and about 2.74 mg.

8. The method of claim 1, wherein the marker has a mass of between about 0.1 mg and about 1.37 mg.

9. The medical device of claim 1, wherein the final ultimate tensile strength is between about 150 KSI and about 200 KSI; and
   wherein the marker has a mass of between about 0.1 mg and about 1.37 mg.

10. The method of claim 1, wherein the final ultimate tensile strength is between about 170 KSI and about 200 KSI; and
    wherein the marker has a mass of between about 0.1 mg and about 1.37 mg.

11. The method of claim 1, wherein the final ultimate tensile strength is between about 172 KSI and about 197 KSI; and
    wherein the marker has a mass of between about 0.1 mg and about 1.37 mg.

12. The method of claim 1, wherein the final ultimate tensile strength is between about 187 KSI and about 191 KSI; and
    wherein the marker has a mass of between about 0.1 mg and about 1.37 mg.

13. The medical device of claim 1, wherein the marker is a tubular member defining a lumen; and
    wherein said medical device comprises a body member that extends into the lumen of the marker.

14. The medical device of claim 13, wherein the body member extends through the lumen of the marker.

15. The medical device of claim 1, wherein said medical device comprises a body member having a thickness and a passageway extending only partially through the thickness; and
    wherein the marker is disposed within the passageway.

16. The medical device of claim 1, wherein said medical device comprises a body member having a thickness and a passageway extending through the entire thickness; and
    wherein the marker is disposed within the passageway.

17. The medical device produced by the method of claim 1.

18. A method of making a medical device useful in interventional procedures performed under magnetic resonance imaging, comprising:
    selecting a medical device precursor;
    selecting a marker stock member formed of stainless steel having a starting ultimate tensile strength;
    separating a portion of the marker stock member from the remainder of the marker stock member to form a marker;
    identifying a final ultimate tensile strength of between about 100 KSI and about 225 KSI for the marker;
    cold working the marker until the marker has a marker ultimate tensile strength that is greater than the starting ultimate tensile strength but less than the final ultimate tensile strength; and
    attaching the marker to the medical device precursor to form said medical device;
    wherein the attaching is performed in a manner that contributes work to the stainless steel of the marker such that the marker in said medical device has substantially the final ultimate tensile strength.

19. The medical device produced by the method of claim 18.

* * * * *